United States Patent [19]
Jungheim et al.

[11] Patent Number: 5,905,077
[45] Date of Patent: May 18, 1999

[54] INHIBITORS OF HIV PROTEASE USEFUL FOR THE TREATMENT OF AIDS

[75] Inventors: Louis N. Jungheim; Timothy A. Shepherd, both of Indianapolis, Ind.

[73] Assignee: Eli Lilly and Company, Indianapolis, Ind.

[21] Appl. No.: 08/974,430

[22] Filed: Nov. 19, 1997

Related U.S. Application Data

[60] Division of application No. 08/134,329, Oct. 12, 1993, Pat. No. 5,733,906, which is a continuation-in-part of application No. 07/995,256, Dec. 22, 1992.

[51] Int. Cl.$^6$ .................... A61K 31/54; A61K 31/495; A61K 31/47; A61K 31/41
[52] U.S. Cl. .................. 514/222.2; 514/252; 514/253; 514/307; 514/361; 514/422; 514/423
[58] Field of Search .................... 514/222.2, 252, 514/253, 307, 361, 422, 423

[56] References Cited

U.S. PATENT DOCUMENTS

| | | | |
|---|---|---|---|
| 5,142,056 | 8/1992 | Kempe et al. | 546/265 |
| 5,312,820 | 5/1994 | Ashton et al. | 514/227.5 |

FOREIGN PATENT DOCUMENTS

| | | |
|---|---|---|
| 0 337714 | 10/1989 | European Pat. Off. . |
| 0 346847 | 12/1989 | European Pat. Off. . |
| 0 361341 | 4/1990 | European Pat. Off. . |
| 0 402646 | 12/1990 | European Pat. Off. . |
| 0 432695 | 6/1991 | European Pat. Off. . |
| 0 498680 | 8/1992 | European Pat. Off. . |
| 0 512343 | 11/1992 | European Pat. Off. . |
| 0 526009 | 2/1993 | European Pat. Off. . |
| WO 92/08701 | 5/1992 | WIPO . |
| WO 93/13066 | 7/1993 | WIPO . |

OTHER PUBLICATIONS

Roberts, N.A. et al., 248, 358–361 (1990).
Vara Prasad, J.V.N. et al., Peptides, Chemistry and Biology, Proceedings of the Twelfth American Peptide Symposium, Jun. 16–21, 721–722 (1991).
Thaisrivongs, s. et al., J. Med. Chem., 34, 2344–2356 (1991).

*Primary Examiner*—Russell Travers
*Attorney, Agent, or Firm*—Birch, Stewart, Kolasch & Birch, LLP

[57] ABSTRACT

The present invention provides novel HIV protease inhibitors, pharmaceutical formulations containing those compounds and methods of treating and/or preventing HIV infection and/or AIDS.

27 Claims, No Drawings

INHIBITORS OF HIV PROTEASE USEFUL FOR THE TREATMENT OF AIDS

This application is a divisional of application Ser. No. 08/134,329, filed on Oct. 12, 1993, now U.S. Pat. No. 5,733,906, which is a continuation-in-part of application Ser. No. 07/995,256 filed on Dec. 22, 1992, the entire contents of which are hereby incorporated by reference.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment of AIDS and the prevention or treatment of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, the currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or short in vivo half-lives. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment or prevention of HIV infection and/or the resulting acquired immune deficiency syndrome (AIDS).

A further object of the present invention is to provide therapeutic compositions that are useful in the treatment or prevention of HIV infection and/or AIDS.

Still another object is to provide methods for the treatment or prevention of HIV infection and/or AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) or type 2 (HIV-2). These compounds are useful in the treatment or prevention of HIV infection and the treatment or prevention of the resulting acquired immune deficiency syndrome (AIDS). The compounds, their pharmaceutically acceptable salts, and the pharmaceutical compositions can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method of inhibiting HIV replication in an HIV infected cell, a cell susceptible to HIV infection or a primate in need thereof, thus treating or preventing HIV infection and/or AIDS, comprising administering an effective amount of a compound of formula I

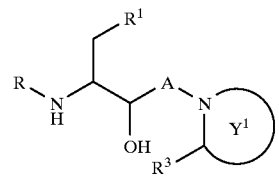

wherein:

R is a group having the formula:

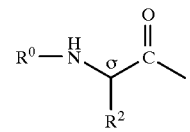

$R^2$ is an amino acid side chain or —$(CH_2)_y$—X—$R^{2a}$;

y is 0, 1 or 2;

X is a bond, divalent($C_2$–$C_4$)alkenyl, divalent ($C_2$–$C_4$) alkynyl, —C(O)—O—, —O—C(O)—, —C(O)—$NR^{2b}$—, —$NR^{2b}$—C(O)—, —$NR^{2b}$—, —C(O)—, —O—, —S—, —S(O)— or —$S(O)_2$;

$R^{2a}$ is aryl, unsaturated heterocycle, heterocycle, aryl ($C_1$–$C_4$)alkyl, unsaturated heterocycle($C_1$–$C_4$)alkyl, heterocycle($C_1$–$C_4$)alkyl, tetrazolyl, N-($C_1$–$C_4$) alkyltetrazolyl or N-(aryl)tetrazolyl;

$R^{2b}$ is hydrogen or $C_1$–$C_4$ alkyl;

$R^0$ is hydrogen, carbamoyl, formyl, $C_2$–$C_6$ alkanoyl, $C_1$–$C_4$ alkoxycarbonyl, —$C(O)CF_3$ or —$S(O)_2$—Z;

Z is $C_1$–$C_6$ alkyl, amino, $C_1$–$C_4$ alkylamino, trifluoromethyl or di($C_1$–$C_4$)alkylamino;

the asymmetric center, σ, is in a non-naturally occurring configuration;

$R^1$ is aryl, $C_5$–$C_7$ cycloalkyl or —S—$R^{1x}$, where $R^{1x}$ is aryl or $C_5$–$C_7$ cycloalkyl;

A is —CH₂— or

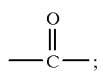

Y¹ is heterocycle;
R³ is a group having the structure:
1) —C(O)—NR⁴R⁴,

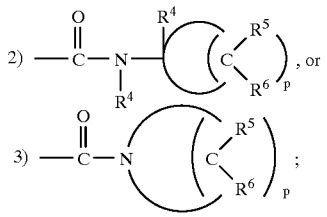

where:
p is 4 or 5;
R⁴ at each occurrence is independently hydrogen, $C_1$–$C_6$ alkyl or hydroxy($C_1$–$C_4$)alkyl; and
R⁵ and R⁶ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkyl, carboxy, $C_1$–$C_4$ alkoxycarbonyl, carbamoyl, N-($C_1$–$C_4$) alkylcarbamoyl, aryl, heterocycle or unsaturated heterocycle; or a pharmaceutically acceptable salt thereof.

The present invention also relates to a compound of formula I, or a pharmaceutically acceptable salt thereof, wherein R, R¹, R³ and Y are as defined above.

The present invention further provides pharmaceutical formulations comprising a compound of the present invention, or a pharmaceutically acceptable salt thereof, in combination with a pharmaceutically acceptable carrier, diluent or excipient therefor.

DETAILED DESCRIPTION OF THE INVENTION

The present invention provides new compounds of formula I, as described above, that are useful for treating or preventing HIV infection and/or AIDS.

All temperatures stated herein are in degrees Celsius (°C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl".

"Divalent($C_2$–$C_4$)alkenyl represents a straight or branched divalent alkenyl chain having from two to four carbon atoms. Typical divalent($C_2$–$C_4$)alkenyl groups include echenyl, 1-propenyl, 2-propenyl, 1-butenyl, 2-butenyl and the like.

"Divalent($C_2$–$C_4$)alkynyl represents a straight or branched divalent alkynyl chain having from two to four carbon atoms. Typical divalent($C_2$–$C_4$)alkynyl groups include ethynyl, 1-propynyl, 2-propynyl, 1-butynyl, 2-butynyl and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Hydroxy($C_1$–$C_4$)alkyl" represents a straight or branched alkyl chain having from one to four carbon atoms with an hydroxy group attached to it. Typical hydroxy($C_1$–C4)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl and the like.

"$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$)alkylamino" represents a straight or branched dialkylamino chain having two alkyl chains, each having independently from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"Carbamoyl($C_1$–$C_4$)alkyl" represents a straight or branched alkyl chain having from one to four carbon atoms with a carbamoyl group attached to it. Typical carbamoyl ($C_1$–$C_4$) alkyl groups include carbamoylmethyl, carbamoylethyl, carbamoylpropyl, carbamoylisopropyl, carbamoylbutyl and carbamoyl-t-butyl and the like.

"N-($C_1$–$C_4$)alkylcarbamoyl" represents a straight or branched alkyl chain having from one to four carbon atoms attached to the nitrogen atom of a carbamoyl moiety. Typical N-($C_1$–$C_4$)alkylcarbamoyl groups include N-methylcarbamoyl, N-ethylcarbamoyl, N-propylcarbamoyl, N-isopropylcarbamoyl, N-butylcarbamoyl, N-t-butylcarbamoyl and the like.

"$C_5$–$C_7$ cycloalkyl" represents a saturated hydrocarbon ring structure containing from five to seven carbon atoms which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or a group having the structure —(CH₂)ₐ—R⁷ where a is 1, 2, 3 or 4 and R⁷ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical $C_5$–$C_7$ cycloalkyl groups include cyclopentyl, cyclohexyl, cycloheptyl, 3-methylcyclopentyl, 4-ethoxycyclohexyl, 5-carboxycycloheptyl, 6-chlorocyclohexyl and the like.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$) alkylcarbamoyl, amino, $C_1$–$C_4$ alkylamino, di($C_1$–$C_4$) alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino, pyridyl or di($C_1$–$C_4$)-alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$) alkylcarbamoyl, amino, $C_1$–$C_4$ alkylamino, di($C_1$–$C_4$) alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methylquinolin-2-yl, 2-t-butoxycarbonyl-1,2,3,4-isoquinolin-7-yl, 4-methylpiperazinyl and the like.

"Unsaturated heterocycle($C_1$–$C_4$)alkyl" represents a straight or branched alkyl chain having from one to four carbon atoms with an unsaturated heterocycle group attached to it. Typical unsaturated heterocycle($C_1$–$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl and the like.

"Heterocycle($C_1$–$C_4$)alkyl" represents a straight or branched alkyl chain having from one to four carbon atoms with a heterocycle group attached to it. Typical heterocycle ($C_1$–$C_4$)alkyl groups include tetrahydrofurylmethyl, tetrahydropyranylmethyl, 1-indolylethyl, 2-tetrahydrisoquinolinylethyl, 3-tetrahydroquinolinylpropyl, morpholinoisopropyl, 4-piperazinylbutyl and the like.

"Aryl" represents a phenyl or naphthyl ring which is optionally substituted with 1, 2 or 3 substituents independently selected from halo, morpholino($C_1$–$C_4$)alkoxy, pyridyl($C_1$–$C_4$)alkoxy, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkyl-amino, di($C_1$–$C_4$)alkylamino or a group of the formula —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical aryl groups include 4-methylphenyl, 3-ethylnaphthyl, 2,5-dimethylphenyl, 8-chloronaphthyl, 3-aminonaphthyl, 4-carboxyphenyl and the like.

"Aryl($C_1$–$C_4$)alkyl" represents a straight or branched alkyl chain having from one to four carbon atoms with an aryl group attached to it. Typical aryl($C_1$–$C_4$)alkyl groups include phenylmethyl, 2-phenylethyl, 3-naphthylpropyl, 1-naphthylisopropyl, 4-phenylbutyl and the like.

The term "non-naturally occurring configuration" refers to stereochemiscry of a substituent, which is derived from a non-naturaily occurring amino acid of the structure:

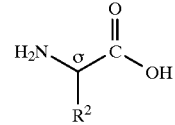

where:

$R^2$ is as defined above for formula I; and the asymmetric center, σ, is in the unnatural orientation.

The term "amino acid side chain" represents the distinctive atom or group bonded to an α-carbon atom also having bonded thereto a carboxyl group and an amino group. These side chains are selected from those found on the following amino acids:

Alanine Ala
Arginine Arg
Asparagine Asn
Aspartic acid Asp
Cysteine Cys
Glutamine Gln
Glutamic acid Glu
Glycine Gly
Histidine His
Isoleucine Ile
Leucine Leu
Lysine Lys
Methionine Met
Phenylalanine Phe
Proline Pro
Serine Ser Threonine Thr
Tryptophan Trp
Tyrosine Tyr
Valine Val The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2 2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamechylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention have at least three asymmetric centers as denoted by the asterisksand σ in the formula below:

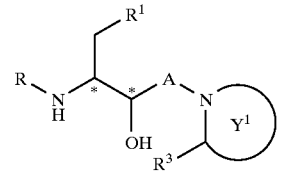

wherein:

R is a group having the structure:

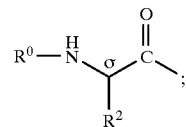

$R^0$, $R^1$, $R^2$, $R^3$, A and $Y^1$ are as defined above in formula I; and the asymmetric center, σ, in the formula above, is in the non-naturally occurring configuration.

As a consequence of these asymmetric centers, the compounds of the present invention occur as racemates, racemic mixtures and as individual enantiomers. All asymmetric forms, individual isomers and combinations thereof, are within the scope of the present invention except the third asymmetric center, σ, must be in the non-natural configuration.

As mentioned above, the invention includes the pharmaceutically acceptable salts of the compounds defined by formula I. Although generally neutral, a compound of this invention can possess a sufficiently-acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formace, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

A is —$CH_2$—;
$R^1$ is aryl or —S—$R^{1x}$, where $R^{1x}$ is aryl;
$Y^1$ is decahydro-(4aS, 8aS)-isoquinolinyl or 2'S-pyrrolidinyl; and
$R^3$ is —C(O)—$NR^4R^4$, where $R^4$ is independently and at each occurrence hydrogen or $C_1$–$C_6$ alkyl;
or a pharmaceutically acceptable salt thereof.

Of these compounds, more preferred are those compounds of formula I where:

$R^1$ is phenyl, phenylthio, naphthyl or naphthylthio;
$R^2$ is —$(CH_2)_y$—X—$R^{2a}$, where
  y is 1;
  X is —S—, —S(O)— or —$S(O)_2$—;
  $R^{2a}$ is aryl, unsaturated heterocycle, aryl($C_1$–$C_4$)alkyl, unsaturated heterocycle($C_1$–$C_4$)alkyl, tetrazolyl, N-($C_1$–$C_4$)alkyltetrazolyl or N-(aryl)tetrazolyl;
$R^0$ is formyl, ethanoyl, —C(O)$CF_3$ or —$S(O)_2$—Z;
  Z is methyl or trifluoromethyl;
$y^1$ is decahydro-(4aS, 8aS)-isoquinolinyl; and
$R^3$ is —C(O)NH(t-butyl);
or a pharmaceutically acceptable salt thereof.

The following list of compounds is provided to further illustrate compounds of formula I included within the scope of the invention:

[2R-(2R*,3R*, 6R*,2'S)]-N(t-butyl) -1'-[2-hydroxy-3-(naphth-2-ylthiomethyl)-4-aza-5,8-dioxo-6-N(t-butoxycarbonyl)amino-8-benzyloxy]octyl 2'-prolinamide;

[2R-(2R*,3R*, 6R*,2'S)]-N(t-butyl)-1'-[2-hydroxy-3-phenylthiomethyl-4-aza-5,8-dioxo-6-N(t-butoxycarbonyl)amino-8-benzyloxy]octyl 2'-prolinamide;

[2R-(2R*,3R*, 6R*,2'S)]-N(t-butyl)-1'-[1-oxo-2-hydroxy-3-phenylthiomethyl-4-aza-5,8-dioxo-6-N(t-butoxycarbonyl)amino-8-benzyloxy]octyl 2'-prolinamide;

[2R-(2R*,3R*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl 2'-prolinamide;

[2R-(2R*,3S*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl 2'-prolinamide;

[2R-(2R*,3R*,6R*,2'S)]-N(t-butyl)-1'-[2-hydroxy-3-(naphth-2-ylthiomethyl)-4-aza-5,8-dioxo-6-N(ethanoyl)amino-8-N(quinolin-2"-yl)amino]octyl 2'-prolinamide;

[2R-(2R*,3R*,6R*,2'S)]-N(t-butyl)-1'-[2-hydroxy-3-(naphth-2-ylthiomethyl)-4-aza-5,8-dioxo-6-N(methylsulfonyl)amino-8-N(naphth-2"-yl)amino]octyl 2'-prolinamide;

[2R-(2R*,3R*,6R*,2'S)]-N(t-butyl)-1'-[2-hydroxy-3-(phenylmethyl)-4-aza-5,8-dioxo-6-N(ethanoyl)amino-8-N(pyrid-2"-ylmethyl)amino]octyl 2'-prolinamide;

[2R-(2R*,3S*,6R*,2'S)]-N(t-butyl)-1'-[2-hydroxy-3-(phenylmethyl)-4-aza-5,8-dioxo-6-N(ethanoyl)amino-8-N(pyrid-2"-ylmethyl)amino]octyl 2'-prolinamide;

[2R-(2R*,3R*,6R*,2'S)]-N(t-butyl)-1'-[2-hydroxy-3-(naphth-2-ylthiomethyl)-4-aza-5,8-dioxo-6-N(propanoyl)amino-8-N(isoquinolin-3"-yl)amino]octyl 2'-prolinamide;

[2R-(2R*,3R*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl 2'-prolinamide;

[2R-(2R*,3S*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl 2'-prolinamide;

[2R-(2R*,3R*,6R*,2'S)]-N(t-butyl)-1'-[2-hydroxy-3-(naphth-2-ylmethyl)-4-aza-5-oxo-6-amino-8-N(pyrid-2"-ylmethyl)amino]octyl 2'-prolinamide;

[2R-(2R*,3S*,6R*,2'S)]-N(t-butyl)-1'-[2-hydroxy-3-(naphth-2-ylmethyl)-4-aza-5-oxo-6-amino-8-N(pyrid-2"-ylmethyl)amino]octyl 2'-prolinamide;

[2R-(2R*,3R*,6S*,2'S)]-N(t-butyl)-1'-[2-hydroxy-3-phenylmethyl-4-aza-5-oxo-6-N(ethanoyl)amino-7-phenylthio]-heptyl 2'-prolinamide;

[2R-(2R*,3S*,6S*,2'S)]-N(t-butyl)-1'-[2-hydroxy-3-phenylmethyl-4-aza-5-oxo-6-N(ethanoyl)amino-7-phenylthio]-heptyl 2'-prolinamide;

[2R-(2R*,3R*,6S*,2'S)]-N(t-butyl)-1'-[2-hydroxy-3-phenylmethyl-4-aza-5-oxo-6-N(ethanoyl)amino-7-quinolin-2"-ylthio]heptyl 2'-prolinamide;

[2R-(2R*,3S*,6S*,2'S)]-N(t-butyl)-1'-[2-hydroxy-3-phenylmethyl-4-aza-5-oxo-6-N(ethanoyl)amino-7-quinolin-2"-ylthio]heptyl 2'-prolinamide;

[2R-(2R*,3R*,6S*,2'S)]-N(t-butyl)-1'-[1-oxo-2-hydroxy-3-(naphth-2-ylthiomethyl)-4-aza-5-oxo-6-N(Ethanoyl)amino-7-naphth-2"-ylsulfinyl]heptyl 2'-prolinamide;

[2R-(2R*,3R*,6S*,2'S)]-N(t-butyl)-1'-[1-oxo-2-hydroxy-3-(naphth-2-ylthiomethyl)-4-aza-5-oxo-6-N(ethanoyl)amino-7-naphth-2"-ylthio]heptyl 2'-prolinamide;

[2R-(2R*,3R*,6S*,2'S)]-N(t-butyl)-1'-[2-hydroxy-3 phenylmethyl-4-aza-5-oxo-6-N(methylsulfonyl)amino-7-quinolin-2"-ylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-phenylsulfinyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-phenylsulfinyl]heptyl 2'-prolinamide;

[2R-(2R*,3R*,6S*,2'S)]-N(t-butyl)-1'-[1-oxo-2-hydroxy-3-phenylthiomethyl-4-aza-5-oxo-6-N(propylsulfonyl)amino-7-quinolin-2-ylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylthio]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-p-fluorophenylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylthio]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-p-fluorophenylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-2"-ylsulfonyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 2'-prolinamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-2"-ylsulfonyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 2'-prolinamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 2'-prolinamide;

[2R-(2R*,3S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl 2'-prolinamide;

[2R-(2R*,3R*,6S*,2'S)]-N(t-butyl)-1'-[2-hydroxy-3-phenylthiomethyl-4-aza-5-oxo-6-N(ethanoyl)amino-7-N(4"-methylpiperazin-1"-ylsulfonyl)]heptyl 2'-prolinamide;

[2R-(2R*,3R*,6R*,2'S)]-N(t-butyl)-1'-[2-hydroxy-3-(naphth-2-ylthiomethyl)-4-aza-5,8-dioxo-6-N(t-butoxycarbonyl)amino-8-benzyloxy]octyl 4'-methyl-piperazin-2'-carboxamide;

[2R-(2R*,3R*,6R*,2'S)]-N(t-butyl)-1'-[2-hydroxy-3-phenylthiomethyl)-4-aza-5,8-dioxo-6-N(t-butoxycarbonyl)amino-8-benzyloxy]octyl 4'-methyl-piperazin-2'-carboxamide;

[2R-(2R*,3R*,6R*,2'R)]-N(t-butyl)-1'-[1-oxo-2-hydroxy-3-phenylthiomethyl-4-aza-5,8-dioxo-6-N(t-butoxycarbonyl)amino-8-benzyloxy]octyl 4'-methyl-piperazin-2'-carboxamide;

[2R-(2R*,3R*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl 4'-methyl-piperazin-2'-carboxamide;

[2R-(2R*,3S*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl 4'-methyl-piperazin-2'-carboxamide;

[2R-(2R*,3R*,6R*,2'R)]-N(t-butyl)-1'-[2-hydroxy-3-(naphth-2-ylthiomethyl)-4-aza-5,8-dioxo-6-N(ethanoyl)amino-8-N(quinolin-2"-yl)amino]octyl 4'-methyl-piperazin-2'-carboxamide;

[2R-(2R*,3R*,6R*,2'R)]-N(t-butyl)-1'-[2-hydroxy-3-(naphth-2-ylthiomethyl)-4-aza-5,8-dioxo-6-N(methylsulfonyl)amino-8-N(naphth-2"-yl)amino]octyl 4'-methyl-piperazin-2'-carboxamide;

[2R-(2R*,3R*,6R*,2'R)]-N(t-butyl)-1'-[2-hydroxy-3-(phenylmethyl)-4-aza-5,8-dioxo-6-N(ethanoyl)amino-8-N(pyrid-2"-ylmethyl)amino]octyl 4'-methyl-piperazin-2'-carboxamide;

[2R-(2R*,3S*,6R*,2'R)]-N(t-butyl)-1'-[2-hydroxy-3-(phenylmethyl)-4-aza-5,8-dioxo-6-N(ethanoyl)amino-8-N(pyrid-2"-ylmethyl)amino]octyl 4'-methyl-piperazin-2'-carboxamide;

[2R-(2R*,3R*,6R*,2'S)]-N(t-butyl)-1'-[2-hydroxy-3-(naphth-2-ylthiomethyl)-4-aza-5,8-dioxo-6-N(propanoyl)amino-8-N(isoquinolin-3"-yl)amino]octyl 4'-methyl-piperazin-2'-carboxamide;

[2R-(2R*,3R*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl 4'-methylpiperazin-2'-carboxamide;

[2R-(2R*,3R*,6R*,2'R)]-N(t-butyl)-1'-[2-hydroxy-3-(naphth-2-ylmethyl)-4-aza-5-oxo-6-amino-8-N(pyrid-2"-ylmethyl)amino]octyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(ethanoyl)amino-7-phenylthio]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(ethanoyl)amino-7-quinolin-2"-ylthio]heptyl 4'-methyl-piperazin-2'-carboxamide;

[2R-(2R*,3S*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl 4'-methylpiperazin-2'-carboxamide;

[2R-(2R*,3S*,6R*,2'R)]-N(t-butyl)-1'-[2-hydroxy-3-(naphth-2-ylmethyl)-4-aza-5-oxo-6-amino-8-N(pyrid-2"-ylmethyl)amino]octyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(ethanoyl)amino-7-phenylthio]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(ethanoyl)amino-7-quinolin-2"-ylthio]heptyl 4'-methyl-piperazin-2'-carboxamide;

[2R-(2R*,3R*,6S*,2'R)]-N(t-butyl)-1'-[1-oxo-2-hydroxy-3-(naphth-2-ylthiomethyl)-4-aza-5-oxo-6-N(ethanoyl)amino-7-naphth-2"-ylsulfinyl]heptyl 4'-methyl-piperazin-2'-carboxamide;

[2R-(2R*,3R*,6S*,2'S)]-N(t-butyl)-1'-[1-oxo-2-hydroxy-3-(naphth-2-ylthiomethyl)-4-aza-5-oxo-6-N(ethanoyl)amino-7-naphth-2"-ylthio]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-phenylsulfinyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-phenylsulfinyl]heptyl 4'-methyl-piperazin-2'-carboxamide;

[2R-(2R*,3R*,6S*,2'R)]-N(t-butyl)-1'-[1-oxo-2-hydroxy-3-phenylthiomethyl-4-aza-5-oxo-6-N(propylsulfonyl)amino-7-quinolin-2"-ylsulfonyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-quinolin-2"-ylthio]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-p-fluorophenylsulfonyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-p-methylphenylsulfonyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-(8"-methylquinolin-2"-ylthio)]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-quinolin-2"-ylthio]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-p-fluorophenylsulfonyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-p-methylphenylsulfonyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-(8"-methylquinolin-2"-ylthio)]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(4"-methylquinolin-2"-ylthio)]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(6"-methylquinolin-2"-ylsulfinyl)]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-2"-ylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(4"-methylquinolin-2"-ylthio)]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(6"-methylquinolin-2"-ylsulfinyl)]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-2"-ylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3R*,6S*,2'S)]-N(t-butyl)-1'-[2-hydroxy-3-phenylthiomethyl-4-aza-5-oxo-6-N(ethanoyl)amino-7-(4"-methylpiperazin-2"-ylsulfonyl)]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-phenylsulfinyl]heptyl 4'-methylpiperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-phenylsulfinyl]heptyl 4'-methylpiperazin-2'-carboxamide;

[2R-(2R*,3R*,6S*,2'S)]-N(t-butyl)-1'-[1-oxo-2-hydroxy-3-phenylthiomethyl-4-aza-5-oxo-6-N(propylsulfonyl)amino-7-quinolin-2"-ylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylthio]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-naphth-2-ylsulfonyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-naphth-2"-ylsulfinyl]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-p-fluorophenylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl 4'-methyl-piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl 4-N(methyl)piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylthio]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-naphth-2-ylsulfonyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-naphth-2"-ylsulfinyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-p-fluorophenylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl 4-N(methyl)piperazin-2'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-pyrid-2"-ylsulfonyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 4'-methyl-piperazin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-pyrid-2"-ylsulfonyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-pyrid-4"-ylthio]heptyl 4'-methyl-piperazin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl 4'-methyl-piperazin-2'-carboxamide;

[2R-(2R*,3R*,6S*,2'R)]-N(t-butyl)-1'-[2-hydroxy-3-phenylthiomethyl-4-aza-5-oxo-6-N(ethanoyl)amino-7-(4"-methyl-piperazin-2"-ylsulfonyl)]heptyl 4'-methyl-piperazin-2'-carboxamide;

[2R-(2R*,3R*,6R*,2'S)]-N(t-butyl)-1'-[2-hydroxy-3-(naphth-2-ylthiomethyl)-4-aza-5,8-dioxo-6-N(t-butoxycarbonyl)amino-8-benzyloxy]octyl piperidin-2'-carboxamide;

[2R-(2R*,3R*,6R*,2'S)]-N(t-butyl)-1'-[2-hydroxy-3-phenylthiomethyl)-4-aza-5,8-dioxo-6-N(t-butoxycarbonyl)amino-8-benzyloxy]octyl piperidin-2'-carboxamide;

[2R-(2R*,3R*,6R*,2'S)]-N(t-butyl)-1'-[1-oxo-2-hydroxy-3-phenylthiomethyl-4-aza-5,8-dioxo-6-N(t-butoxycarbonyl)amino-8-benzyloxy]octyl piperidin-2'-carboxamide;

[2R-(2R*,3R*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl piperidin-2'-carboxamide;

[2R-(2R*,3S*,6R*,2'S)]-N(t-butyl)-1'-[1-oxo-2-hydroxy-3-phenylmethyl-4-aza-5,8-dioxo-6-N(t-butoxycarbonyl)amino-8-benzyloxy]octyl piperidin-2'-carboxamide;

[2R-(2R*,3R*,6R*,2'S)]-N(t-butyl)-1'-[2-hydroxy-3-(naphth-2-ylthiomethyl)-4-aza-5,8-dioxo-6-N(ethanoyl)amino-8-N(quinolin-2"-yl)amino]octyl piperidin-2'-carboxamide;

[2R-(2R*,3R*,6R*,2'S)]-N(t-butyl)-1'-[2-hydroxy-3-(naphth-2-ylthiomethyl)-4-aza-5,8-dioxo-6-N(methylsulfonyl)amino-8-N(naphth-2"-yl)amino]octyl piperidin-2'-carboxamide;

[2R-(2R*,3R*,6R*,2'S)]-N(t-butyl)-1'-[2-hydroxy-3-(phenylmethyl)-4-aza-5,8-dioxo-6-N(ethanoyl)amino-8-N(pyrid-2"-ylmethyl)amino]octyl piperidin-2'-carboxamide;

[2R-(2R*,3S*,6R*,2'S)]-N(t-butyl)-1'-[2-hydroxy-3-(phenylmethyl)-4-aza-5,8-dioxo-6-N(ethanoyl)amino-8-N(pyrid-2"-ylmethyl)amino]octyl piperidin-2'-carboxamide;

[2R-(2R*,3R*,6R*,2'S)]-N(t-butyl)-1'-[2-hydroxy-3-(naphth-2-ylthiomethyl)-4-aza-5,8-dioxo-6-N(propanoyl)-amino-8-N(isoquinolin-3"-yl)amino]octyl piperidin-2'-carboxamide;

[2R-(2R*,3R*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl piperidin-2'-carboxamide;

[2R-(2R*,3R*,6R*,2'S)]-N(t-butyl)-1'-[2-hydroxy-3-(naphth-2-ylmethyl)-4-aza-5-oxo-6-amino-8-N(pyrid-2"-ylmethyl)amino]octyl piperidin-2'-carboxamide;

[2R-(2R*,3R*,6S*,2'S)]-N(t-butyl)-1'-[2-hydroxy-3-phenylmethyl-4-aza-5-oxo-6-N(ethanoyl)amino-7-phenylthio]heptyl piperidin-2'-carboxamide;

[2R-(2R*,3R*,6S*,2'S)]-N(t-butyl)-1'-[2-hydroxy-3-phenylmethyl-4-aza-5-oxo-6-N(ethanoyl)amino-7-quinolin-2"-ylthio]heptyl piperidin-2'-carboxamide;

[2R-(2R*,3S*,6R*,2'S)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl piperidin-2'-carboxamide;

[2R-(2R*,3S*,6R*,2'S)]-N(t-butyl)-1'-[2-hydroxy-3-(naphth-2-ylmethyl)-4-aza-5-oxo-6-amino-8-N(pyrid-2"-ylmethyl)amino]octyl piperidin-2'-carboxamide;

[2R-(2R*,3S*,6S*,2'S)]-N(t-butyl)-1'-[2-hydroxy-3-phenylmethyl-4-aza-5-oxo-6-N(ethanoyl)amino-7-phenylthio]heptyl piperidin-2'-carboxamide;

[2R-(2R*,3S*,6S*,2'S)]-N(t-butyl)-1'-[2-hydroxy-3-phenylmethyl-4-aza-5-oxo-6-N(ethanoyl)amino-7-quinolin-2"-ylthio]heptyl piperidin-2'-carboxamide;

[2R-(2R*,3R*,6S*,2'S)]-N(t-butyl)-1'-[1-oxo-2-hydroxy-3-(naphth-2-ylthiomethyl)-4-aza-5-oxo-6-N(ethanoyl)amino-7-naphth-2"-ylsulfinyl]heptyl piperidin-2'-carboxamide;

[2R-(2R*,3R*,6S*,2'S)]-N(t-butyl)-1'-[1-oxo-2-hydroxy-3-(naphth-2-ylthiomethyl)-4-aza-5-oxo-6-N(ethanoyl)amino-7-naphth-2"-ylthio]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-phenylsulfinyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-phenylsulfinyl]heptyl piperidin-2'-carboxamide;

[2R-(2R*,3R*,6S*,2'S)]-N(t-butyl)-1'-[1-oxo-2-hydroxy-3-phenylthiomethyl-4-aza-5-oxo-6-N(propylsulfonyl)amino-7-quinolin-2"-ylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-quinolin-2"-ylthio]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-p-fluorophenylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-2"-ylsulfonyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-3"-ylsulfinyl]heptyl piperidin-2'-carboxamide;

[2R-(2R*,3R*,6S*,2'S)]-N(t-butyl)-1'-[2-hydroxy-3-phenylmethyl-4-aza-5-oxo-6-N(methylsulfonyl)amino-7-pyrid-4"-ylthio]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylsulfonyl]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-quinolin-2"-ylthio]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfonyl]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-naphth-2"-ylsulfinyl]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-p-fluorophenylsulfonyl]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-p-methylphenylsulfonyl]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl piperidin-2'-carboxamide;

[2R-(2R*,3S*,6S*,2'S)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl piperidin-2'-carboxamide;

[2R-(2R\*,3S\*,6S\*,2'S)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl piperidin-2'-carboxamide;

[2R-(2R\*,3S\*,6S\*,2'S)]-N(t-butyl)-1'-[2-hydroxy-3-phenylmethyl-4-aza-5-oxo-6-N(methylsulfonyl)amino-7-pyrid-2"-ylsulfonyl]heptyl piperidin-2'-carboxamide;

[2R-(2R\*,3S\*,6S\*,2'S)]-N(t-butyl)-1'-[2-hydroxy-3-phenylmethyl-4-aza-5-oxo-6-N(methylsulfonyl)amino-7-pyrid-3"-ylsulfinyl]heptyl piperidin-2'-carboxamide;

[2R-(2R\*,3S\*,6S\*,2'S)]-N(t-butyl)-1'-[2-hydroxy-3-phenylmethyl-4-aza-5-oxo-6-N(methylsulfonyl)amino-7-pyrid-4"-ylthio]heptyl piperidin-2'-carboxamide;

[2R-(2R\*,3S\*,6S\*,2'S)]-N(t-butyl)-1'-[2-hydroxy-3-phenylmethyl-4-aza-5-oxo-6-N(methylsulfonyl)amino-7-quinolin-2"-ylsulfonyl]heptyl piperidin-2'-carboxamide;

[2R-(2R\*,3R\*,6S\*,2'S)]-N(t-butyl)-1'-[2-hydroxy-3-phenylthiomethyl-4-aza-5-oxo-6-N(ethanoyl)amino-7-(4"-methylpiperazin-2"-ylsulfonyl)]heptyl piperidin-2'-carboxamide;

[2R-(2R\*,3R\*,6R\*,5'R)]-N(t-butyl)-1'-[2-hydroxy-3-(naphth-2-ylthiomethyl)-4-aza-5,8-dioxo-6-N(t-butoxycarbonyl)amino-8-benzyloxy]octyl thiazolidin-5'-carboxamide;

[2R-(2R\*,3R\*,6R\*,5'R)]-N(t-butyl)-1'-[2-hydroxy-3-phenylthiomethyl)-4-aza-5,8-dioxo-6-N(t-butoxycarbonyl)amino-8-benzyloxy]octyl thiazolidin-5'-carboxamide;

[2R-(2R\*,3R\*,6R\*,5'R)]-N(t-butyl)-1'-[1-oxo-2-hydroxy-3-phenylthiomethyl-4-aza-5,8-dioxo-6-N(t-butoxycarbonyl)amino-8-benzyloxy]octyl thiazolidin-5'-carboxamide;

[2R-(2R\*,3R\*,6R\*,5'R)]-N(t-butyl)-1'-[1-oxo-2-hydroxy-3-phenylmethyl-4-aza-5,8-dioxo-6-N(t-butoxycarbonyl)amino-8-benzyloxy]octyl thiazolidin-5'-carboxamide;

[2R-(2R\*,3S\*,6R\*,5'R)]-N(t-butyl)-1'-[1-oxo-2-hydroxy-3-phenylmethyl-4-aza-5,8-dioxo-6-N(t-butoxycarbonyl)amino-8-benzyloxy]octyl thiazolidin-5'-carboxamide;

[2R-(2R\*,3R\*,6R\*,5'R)]-N(t-butyl)-1'-[2-hydroxy-3-(naphth-2-ylthiomethyl)-4-aza-5,8-dioxo-6-N(ethanoyl)amino-8-N(quinolin-2"-yl)amino]octyl thiazolidin-5'-carboxamide;

[2R-(2R\*,3R\*,6R\*,5'R)]-N(t-butyl)-1'-[2-hydroxy-3-(naphth-2-ylthiomethyl)-4-aza-5,8-dioxo-6-N(methylsulfonyl)amino-8-N(naphth-2"-yl)amino]octyl thiazolidin-5'-carboxamide;

[2R-(2R\*,3R\*,6R\*,5'R)]-N(t-butyl)-1'-[2-hydroxy-3-(phenylmethyl)-4-aza-5,8-dioxo-6-N(ethanoyl)amino-8-N(pyrid-2"-ylmethyl)amino]octyl thiazolidin-5'-carboxamide;

[2R-(2R\*,3S\*,6R\*,5'R)]-N(t-butyl)-1'-[2-hydroxy-3-(phenylmethyl)-4-aza-5,8-dioxo-6-N(ethanoyl)amino-8-N(pyrid-2"-ylmethyl)amino]octyl thiazolidin-5'-carboxamide;

[2R-(2R\*,3R\*,6R\*,5'R)]-N(t-butyl)-1'-[2-hydroxy-3-(naphth-2-ylthiomethyl)-4-aza-5,8-dioxo-6-N(propanoyl)amino-8-N(isoquinolin-3"-yl)amino]octyl thiazolidin-5'-carboxamide;

[2R-(2R\*,3R\*,6R\*,5'R)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl thiazolidin-5'-carboxamide;

[2R-(2R\*,3R\*,6R\*,5'R)]-N(t-butyl)-1'-[2-hydroxy-3-(naphth-2-ylmethyl)-4-aza-5-oxo-6-amino-8-N(pyrid-2"-ylmethyl)amino]octyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(ethanoyl)amino-7-phenylthio]-heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(ethanoyl)amino-7-quinolin-2"-ylthio]heptyl thiazolidin-5'-carboxamide;

[2R-(2R\*,3S\*,6R\*,5'R)]-N(t-butyl)-1'-[1-oxo-2-hydroxy-3-phenylmethyl-4-aza-5,8-dioxo-6-N(ethanoyl)-amino-8-N(pyrid-2"-ylmethyl)amino]octyl thiazolidin-5'-carboxamide;

[2R-(2R\*,3S\*,6R\*,5'R)]-N(t-butyl)-1'-[2-hydroxy-3-(naphth-2-ylmethyl)-4-aza-5-oxo-6-amino-8-N(pyrid-2"-ylmethyl)amino]octyl thiazolidin-5'-carboxamide;

[2R-(2R\*,3S\*,6S\*,5'R)]-N(t-butyl)-1'-[2-hydroxy-3-phenylmethyl-4-aza-5-oxo-6-N(ethanoyl)amino-7-phenylthio]-heptyl thiazolidin-5'-carboxamide;

[2R-(2R\*,3S\*,6S\*,5'R)]-N(t-butyl)-1'-[2-hydroxy-3-phenylmethyl-4-aza-5-oxo-6-N(ethanoyl)amino-7-quinolin-2"-ylthio]heptyl thiazolidin-5'-carboxamide;

[2R-(2R\*,3R\*,6S\*,5'R)]-N(t-butyl)-1'-[1-oxo-2-hydroxy-3-(naphth-2-ylthiomethyl)-4-aza-5-oxo-6-N(ethanoyl)amino-7-naphth-2"-ylsulfinyl]heptyl thiazolidin-5'-carboxamide;

[2R-(2R\*,3R\*,6S\*,5'R)]-N(t-butyl)-1'-[1-oxo-2-hydroxy-3-(naphth-2-ylthiomethyl)-4-aza-5-oxo-6-N(ethanoyl)amino-7-naphth-2"-ylthio]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-quinolin-2"-ylsulfonyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-phenylsulfinyl]heptyl thiazolidin-5'-carboxamide;

[2R-(2R\*,3S\*,6S\*,5'R)]-N(t-butyl)-1'-[2-hydroxy-3-phenylmethyl-4-aza-5-oxo-6-N(methylsulfonyl)amino-7-quinolin-2"-ylsulfonyl]heptyl thiazolidin-5'-carboxamide;

[2R-(2R\*,3S\*,6S\*,5'R)]-N(t-butyl)-1'-[2-hydroxy-3-phenylmethyl-4-aza-5-oxo-6-N(methylsulfonyl)amino-7-phenylsulfinyl]heptyl thiazolidin-5'-carboxamide;

[2R-(2R\*,3R\*,6S\*,5'R)]-N(t-butyl)-1'-[1-oxo-2-hydroxy-3-phenylthiomethyl-4-aza-5-oxo-6-N(propylsulfonyl)amino-7-quinolin-2"-ylsulfonyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-quinolin-2"-ylthio]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-naphth-2"-ylsulfonyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-naphth-2"-ylsulfinyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)-amino-7-p-fluorophenylsulfonyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-p-methylphenylsulfonyl]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl thiazolidin-5'-carboxamide;

[2R-(2R\*,3R\*,6S\*,5'R)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl thiazolidin-5'-carboxamide;

[2R-(2R*,3R*,6S*,5'R)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl thiazolidin-5'-carboxamide;

[2R-(2R*,3R*,6S*,5'R)]-N(t-butyl)-1'-[2-hydroxy-3-phenylmethyl-4-aza-5-oxo-6-N(methylsulfonyl)amino-7-pyrid-2"-ylsulfonyl]heptyl thiazolidin-5'-carboxamide;

[2R-(2R*,3R*,6S*,2'R)]-N(t-butyl)-1'-[2-hydroxy-3-phenylmethyl-4-aza-5-oxo-6-N(methylsulfonyl)amino-7-pyrid-3"-ylsulfinyl]heptyl thiazolidin-5'-carboxamide;

[2R-(2R*,3R*,6S*,5'R)]-N(t-butyl)-1'-[2-hydroxy-3-phenylmethyl-4-aza-5-oxo-6-N(methylsulfonyl)amino-7-pyrid-4"-ylthio]heptyl thiazolidin-5'-carboxamide;

[2R-(2R*,3R*,6S*,5'R)]-N(t-butyl)-1'-[2-hydroxy-3-phenylmethyl-4-aza-5-oxo-6-N(methylsulfonyl)amino-7-quinolin-2"-ylsulfonyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-quinolin-2"-ylthio]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-naphth-2"-ylsulfonyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-naphth-2"-ylsulfinyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-p-fluorophenylsulfonyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-p-methylphenylsulfonyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-(8"-methylquinolin-2"-ylsulfonyl)]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-(4"-methylquinolin-2"-ylsulfonyl)]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-(6"-methylquinolin-2"-ylsulfonyl)]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-pyrid-2"-ylsulfonyl]heptyl thiazolidin-5'-carboxamide;

[2R-(2R*,3S*,6S*,2'R)]-N(t-butyl)-1'-[2-hydroxy-3-phenylmethyl-4-aza-5-oxo-6-N(methylsulfonyl)amino-7-pyrid-3"-ylsulfinyl]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-pyrid-4"-ylthio]heptyl thiazolidin-5'-carboxamide;

[2R-(2R*,3S*,6S*,5'R)]-N(t-butyl)-1'-[2-hydroxy-3-phenylmethyl-4-aza-5-oxo-6-N(methylsulfonyl)amino-7-quinolin-2"-ylsulfonyl]heptyl thiazolidin-5'-carboxamide;

[2R-(2R*,3R*,6S*,5'R)]-N(t-butyl)-1'-[2-hydroxy-3-phenylthiomethyl-4-aza-5-oxo-6-N(ethanoyl)amino-7-(4"-methyl-piperazin-2"-ylsulfonyl)]heptyl thiazolidin-5'-carboxamide;

The compounds of the present invention can be prepared according to the procedures shown below in Reaction I.

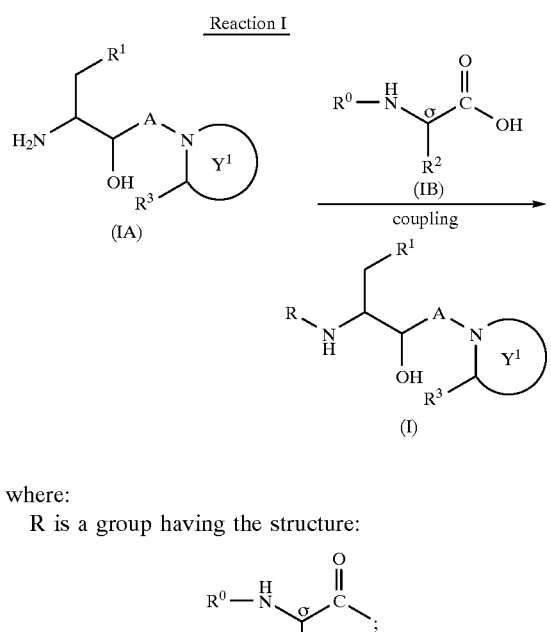

where:

R is a group having the structure:

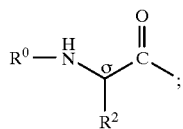

A, $R^0$, $R^1$, $R^2$, $R^3$ and $Y^1$ are as defined above for formula I; and the asymmetric center, σ, is in a non-naturally occurring configuration.

The compounds of formula I may be obtained from reaction I, above. Once the reaction is complete, the compound may be isolated, if desired, by procedures known in the art, for example, the compound may be crystallized and then collected by filtration, or the reaction solvent may be removed by extraction, evaporation or decantation. The compound may be further purified, if desired, by common techniques such as crystallization or chromatography over solid supports such as silica gel or alumina, before carrying out the next step of the reaction scheme.

Reaction I is a standard coupling reaction commonly employed in the synthesis of peptides which is carried out by reacting an appropriately substituted amine of formula IA, with-an appropriately substituted carboxylic acid reactant of formula IB, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, preferably a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.$H_2O$).

Alternatively, compounds of formula I, where $R^0$ is carbamoyl, formyl, $C_2$–$C_6$ alkanoyl, $C_1$–$C_4$ alkoxycarbonyl or —S(O)$_2$—Z, and Z is as defined above for formula I, can be prepared by reacting an amine of formula IA:

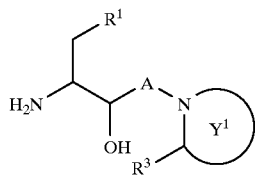
(IA)

with a compound having the formula,

R$^b$—NH—CH(R$^2$)—COOH where:
R$^1$, R$^2$, R$^3$, A and Y$^1$ is as defined above; and
R$^b$ is an amino-protecting group.

The amino-protecting group is then removed from the resulting compound according to procedures and methods known in the art to provide the compound of formula I, where R$^0$ is hydrogen. The resulting compound is then acylated or sulfonylated using procedures known in the art. For example, the amine compounds may be acylated by reaction with a suitable acyl halide, isocyanate or chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride. The amine compounds may be sulfonylated by reaction with a suitably substituted sulfonyl halide of the formula, Z—SO$_2$-halide in an aprotic solvent at a temperature from about −30° C. to about 25° C. in an aprotic solvent such as tetrahydrofuran. The amine reactant is generally employed in equimolar proportions relative to the sulfonyl halide reactant, and preferably in the presence of an acyl transfer catalyst. A preferred acyl transfer catalyst for this reaction is N-methylmorpholine (NMM).

Compounds of formula I, wherein R$^2$ is —(CH$_2$)$_y$—X—R$^{2a}$, where y and R$^{2a}$ are as defined above; and X is —C(O)—NR$^{2b}$—, can be prepared by reacting the amine of formula IA:

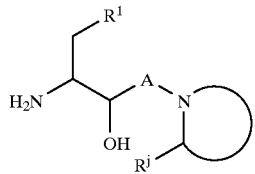
(IA)

with a compound having the formula,

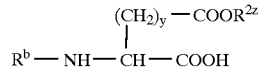

where:
R$^1$, R$^3$, A, Y, R$^b$ and y are as defined above; and
R$^{2z}$ is a carboxy-protecting group.

The carboxy-protecting group is then removed and the resultant compound is reacted with a suitably substituted amine reactant of the formula, H—NR$^{2a}$R$^{2b}$, substantially in accordance with the procedure detailed in Reaction I. A preferred solvent for this reaction is a mixture of tetrahydrofuran and dimethylformamide. A preferred coupling reagent for this reaction is DCC. A preferred promoting agent is HOBT.H$_2$O. The amino-protecting group is then removed from the resultant compound according to procedures and methods known in the art to provide a compound of formula I where R$^0$ is hydrogen, which can then be acylated or sulfonylated using procedures known in the art. For example, the amine compounds may be acylated by reaction with a suitable acyl halide, isocyanate chloroformate, preferably in the presence of an acid scavenger such as a tertiary amine, preferably triethylamine. The reaction is carried out at a temperature of from about −20° C. to about 25° C. Typical solvents for this reaction include ethers and chlorinated hydrocarbons, preferably diethylether, chloroform or methylene chloride. The amine compounds may be sulfonylated by reaction with a suitably substituted sulfonyl halide of the formula, Z—SO$_2$-halide as described above.

Further, a compound of formula I, wherein R$^2$ is —(CH$_2$)$_y$—X—R$^{2a}$, where y and R$^{2a}$ are as defined above; and X is —S(O)— or —S(O)$_2$— may be prepared by oxidizing an intermediate compound of formula IB

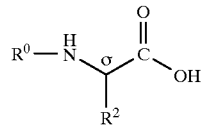
(IB)

where:
R$^2$ is —(CH$_2$)$_y$—X—R$^{2a}$, where
y, R$^0$ and R$^{2a}$ are as defined above; and
X is —S—.;

under standard reaction conditions known in the art. For example, the intermediate compound using X is —S— may be combined with an oxidizing agent in an aqueous or organic solvent at a temperature of from about −78° C. to 25° C. Solvent choice is not critical so long as the solvent employed is inert to the ongoing reaction and the reactants are sufficiently solubilized to effect the desired reaction. Typical oxidizing agents include oxone®, m-chloroperoxybenzoic acid. A preferred oxidizing agent is oxone®.

The compounds of formula IA can be prepared according to the procedures shown below in Reaction Scheme A.

Reaction Scheme A

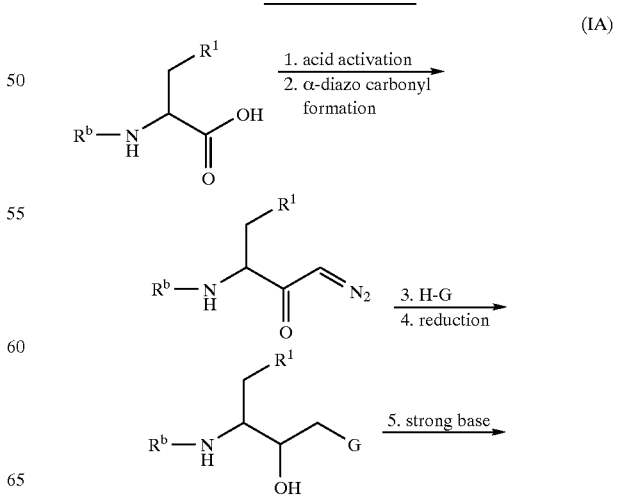

-continued

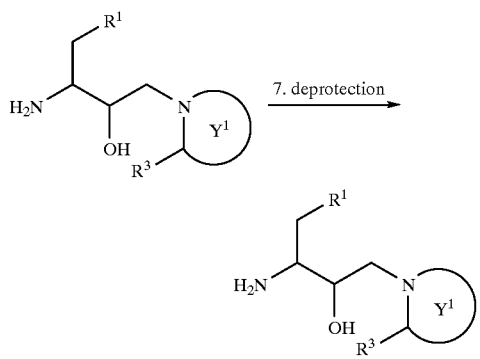

where:

R$^1$, R$^3$, R$^b$ and Y$^1$ are as defined above; and

G is halo.

Reaction Scheme A, above, is accomplished by carrying out reactions 1–7 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction A.1 is carried out by activating, that is, converting, an amino-protected carboxylic acid reactant having the structure:

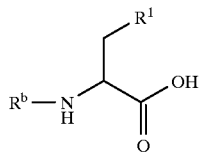

to the corresponding mixed anhydride under conditions known in the art. For example, the amino-protected carboxylic acid reactant may be reacted with a $C_1$–$C_6$ alkylchloroformate, such as isobutylchloroformate. The reaction is preferably carried out in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethylether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1, above, to form the corresponding α-diazo carbonyl compound. The diazomethane reactant is preferably used in this reaction without isolation or purification. The reaction is typically carried out at a temperature of from about –50° C. to about –20° C., preferably about –30° C.

In Reaction A.3, the α-diazo carbonyl compound prepared in Reaction A.2 is reacted with an acid of the formula H–G where G is halo, in an aprotic solvent such as diethylether to form an α-halo carbonyl compound. A preferred acid reactant is hydrochloric acid which provides the corresponding α-chloro carbonyl compound. The reaction is typically carried out at a temperature from about –30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by TLC.

In Reaction A.4, the carbonyl moiety on the compound prepared in Reaction A.3 is reduced using standard conditions known in the art to form the corresponding α-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride and sodium bis(2-methoxyethoxy)aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about –10° C. to about 10° C., preferably about 0° C.

In Reaction A.5, the α-chloro hydroxy compound prepared in Reaction A.4 is treated with a strong base to form the corresponding epoxide under standard conditions known in the art. For example, the α-chloro hydroxy compound may be reacted with a potassium hydroxide/ethanol mixture in an organic solvent such as ethyl acetate. Solvent choice is not critical so long as the solvent employed is inert to the ongoing reaction and the reactants are sufficiently solubilized to effect the desired reaction. The reaction is typically carried out at a temperature from about 0° C. to about the reflux temperature of the solvent. Preferably the reaction is carried out at room temperature.

In Reaction A.6, the epoxide prepared in Reaction A.5 is reacted with a heterocyclic reactant of the formula:

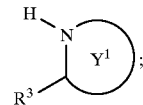

where R$^3$ and Y$^1$ are as defined above in formula I, in a protic solvent at a temperature of from about 70° C. to 100° C. Solvent choice is not critical so long as the solvent employed is inert to the ongoing reaction and the reactants are sufficiently solubilized to effect the desired reaction. Typical solvents for this reaction include the alcohols, preferably ethanol. The reaction is preferably carried out at a temperature of about 80° C.

Reaction A.7 is a standard amino deprotection reaction using procedures and methods known in the art to afford the corresponding amine which is used in Reaction I, above. This amine may be reacted without purification, but it is preferably purified first.

The compounds of formula IA, where $R^1$ is $S-R^{1x}$, where $R^{1x}$ is aryl or $C_5-C_7$ cycloalkyl, are prepared with an amino-protected amino acid reactant having the following structure:

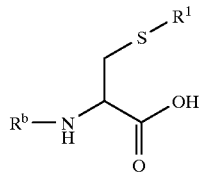

where $R^1$ and $R^b$ are as defined above.

These compounds may be prepared substantially in accordance with the reaction scheme described in Vederas et al., J.Am.Chem. Soc., 107, 7105–7109 (1985). In particular, this reaction scheme is carried out by first reacting amino-protected serine with triphenylphosphine, dimethylazodicarboxylate (DMAD) or diethylazodicarboxylate (DEAD) in an aprotic solvent at a temperature of from about −80° C. to 0° C. to form the corresponding β-lactone. The reaction is typically carried out in an ether, such as tetrahydrofuran at a temperature of from about −80° C. to −50° C. Next, the lactone ring is opened with an appropriately substituted thio anion, $-S-R^1$, where $R^1$ is as defined above. The thio anion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran.

Alternatively, the compounds of formula IA, where $R^1$ is —S-aryl, may be prepared using the procedures detailed in Photaki, J. Am. Chem. Soc., 85, 1123 (1963), and Sasaki, N. A. et al, Tetrahedron Letters, 28, 6069 (1987). For example, the compounds may be prepared by reacting doubly protected serine (carboxy-protected and amino-protected) with toluenesulfonyl chloride in the presence of dimethylaminopyridine (DMAP) and an acid scavenger such as pyridine in an aprotic solvent such as methylene chloride to form the corresponding toluenesulfonate which may then be reacted with an appropriately substituted thioanion having the structure, —S-aryl. The thioanion compound is preferably formed by reacting the corresponding thiol with a strong base as described above. The carboxy-protecting group may be removed from the resulting doubly protected arylthioalanine using conditions known in the art.

The compounds of formula IA where A is

can be prepared according to procedures known in the art. One reference that may be particularly helpful in preparing such compounds is R. Herranz et al., *J. Org. Chem.*, 55, pp 2232–2234 (1990).

The heterocyclic reactants, used in Reaction C.6 above, of the formula

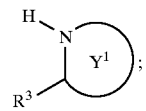

can be prepared using procedures and methods known in the art. For example, the heterocyclic reactants were typically prepared from the corresponding amino-protected amino acids by acid activation followed by treatment with an alkylamine. This reaction is typically carried out in the presence of an acid scavenger, such as N-methylmorpholine. Removal of the amino-protecting group using standard chemical deprotecting techniques then provides the heterocyclic reactants used above in Reaction C.8.

For example, the (3S-(3R*,4aR*,8aR*)]-decahydroisoquinoline-3-N-t-butylcarboxamide was prepared using (2S)-1,2,3,4-tetrahydro-3-isoquinolinecarboxylic acid and the following procedure:

1) amino-protection (t-Boc);
2) acid activation/reaction with t-butylamine;
3) catalytic hydrogenation; and
4) amino-deprotection.

The piperazine reactants may be prepared by converting an appropriately substituted pyrazine compound to the corresponding piperazine compound using procedures known in the art, preferably using catalytic hydrogenation. For example, the hydrogenation may be accomplished by combining the pyrazine reactant with a catalyst under a hydrogen atmosphere in an aprotic solvent at a temperature from about 0° C. to about 60° C. Suitable catalysts include palladium-on-carbon, platinum metal, platinum oxide and the like. A preferred catalyst is platinum oxide. Typical solvents for this reaction include tetrahydrofuran, dimethylformamide or a mixture of tetrahydrofuran and dimethylformamide.

The nitrogen atom on the resultant piperazine reactant may be alkylated using procedures known in the art. For example, the piperazine reactant may be reacted with a halo($C_1-C_4$)alkyl, or halomethylpyridine, such as methyl iodide or chloromethylpyridine. Preferred halo substituents include chloro, bromo and iodo. The reaction is carried out at temperatures of from about 0° C. to 60° C. in a mutually inert solvent and in the presence of an acid scavenger. A preferred acid scavenger is potassium carbonate. Typical solvents include a mixture of a protic and aprotic solvents such as acetonitrile and water. Solvent choice is not critical so long as the solvent employed is inert to the ongoing reaction and the reactants are sufficiently solubilized to effect the desired reaction.

Alternatively, the alkylated piperazine reactant may be prepared using reductive aminacion. For example, the piperazine reactant prepared above may be reacted with an aldehyde (for example, 3-pyridine carboxylic aldehyde, ethanal, propanal) or a ketone in the presence of a reducing agent and an acid. The reaction is typically carried out in an alcoholic solvent such as methanol, ethanol or isopropanol. Typical reducing agents include sodium borohydride, lithium cyanoborohydride, sodium cyanoborohydride, and the like. A preferred reducing agent is sodium cyanoborohydride. Typical acids include any protic acid such as hydrochloric acid, sulfuric acid, methanesulfonic acid, or acetic acid. A preferred acid is acetic acid.

The carboxylic acid reactants used in the coupling reaction described in Reaction I, to the extent not commercially available, can be prepared using procedures known in the art. For example, the carboxylic acid reactants with "D" stereochemistry may be prepared substantially in accordance with the Vederas reaction scheme or the procedures detailed in Photaki and Sasaki, as described above.

It will be understood by those skilled in the art that in performing the processes described above it may be desirable to introduce chemical protecting groups into the reactants in order to prevent secondary reactions from taking place. Any amine, alkylamine or carboxy groups which may be present on the reactants may be protected using any standard amino- or carboxy-protecting group which does not adversely affect the remainder of the molecule's ability to react in the manner desired. The various protective groups may be removed simultaneously or successively using methods known in the art.

As noted above, all asymmetric forms, individual isomers and combinations thereof are considered part of this invention except that the third asymmetric center, σ, must be in the non-natural configuration. Such isomers may be prepared from their respective precursors by the procedures described above, by resolving the racemic mixtures or by separating diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting material in the synthesis of the compounds of this invention are known, and to the extent not commercially available are readily synthesized by standard procedures commonly employed by those in the art.

The pharmaceutically acceptable salts of the invention are typically formed by reacting a compound of formula I with an equimolar or excess amount of acid or base. The reactants are generally combined in a mutual solvent such as diethylether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS (FD)", "MS (FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Bruker Corp. 270 MHz instrument or on a General Electric QE-300 300 MHz instrument. The chemical shifts are expressed in delta (δ) values (parts per million downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

PREPARATION 1

A. (2R)-N(Benzyloxycarbonyl)amino-3-naphth-2-ylthio propanoic acid

To a solution of 1.28 g (8.00 mmol) of naphthalene-2-thiol in 30 mL tetrahydrofuran, was slowly added 1.77 g (8.16 g) of 60% sodium hydride, under nitrogen. After stirring for approximately 15 minutes, N(benzyloxycarbonyl)serine-β-lactone in 20 mL of tetrahydrofuran was slowly added. The reaction mixture was allowed to react at room temperature for approximately one hour, and then was concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid.

Yield: 68%.

$^1$H NMR (CDCl$_3$): δ3.42–3.61 (br.m, 2H), 5.53–5.76 (br.s, 1H), 4.85–5.08 (br.m, 2H), 5.54–5.76 (br.s, 1H), 7.06–7.97 (m, 12H).

$[\alpha]_D$–55.72° (c 1.0, MeOH).

IR (KBr): 3348, 3048, 1746, 1715, 1674, 1560, 1550, 1269, 1200, 1060 cm$^{-1}$.

MS (FD): m/e 381 (M$^+$), 381 (100).

Analysis for C$_{20}$H$_{19}$NO$_4$S: Calcd: C, 66.12; H, 5.02; N, 3.67; Found: C, 66.22; H, 5.04; N, 3.86.

B. (3R) Benzyl 2-aza-3-(naphth-2-ylthiomethyl)-4-oxo-5-diazo pentanoate

To a cold (–30° C.) solution of 15.38 g (40.3 mmol) of the subtitled intermediate from Preparation 1A in 230 mL of ethyl acetate and under nitrogen, was slowly added 5.62 mL (40.3 mmol) of triethylamine, via syringe. To the resulting solution was then added 7.84 mL (60.5 mmol) of isobutyl chloroformate, via syringe. In a separate flask, 10 g of N(methyl)-N(nitro)-N(nitroso)guanidine was carefully added to a bilayer mixture of 170 mL of diethylether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethylether and sodium hydroxide and 30 g of N(methyl)-N(nitro)-N(nitroso)guanidine. The resultant diazomethane reactant was then added to the mixed anhydride solution prepared above and the reaction mixture was allowed to react cold (–30° C.) for approximately 20 minutes. When the reaction was substantially complete, as indicated by TLC, nitrogen was bubbled through the solution using a fire polished Pasteur pipet to remove any excess diazomethane and then the solution was concentrated under reduced pressure to provide a residue. This residue was purified using flash chromatography (eluent of 10% ethyl acetate in methylene chloride) to provide 13.62 g of a yellow oil.

Yield: 83%.

$^1$H NMR (CDCl$_3$): δ3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. (3R) Benzyl 2-aza-3-(naphth-2-ylthiomethyl)-4-oxo-5-chloro pentanoate

A short burst (about 2 seconds) of anhydrous hydrochloric acid (gas) was passed through a cold (−20° C.) solution of 13.62 g (33.59 mmol) of the subtitled intermediate from Preparation 1B in 230 mL of diethylether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid.

Yield: 87%.

$^1$H NMR (CDCl$_3$): δ3.41 (dd, J=12,6 Hz, 1H), 3.53 (dd, J=12,6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (complex, 12H).

[α]$_D$ −80.00° (c 1.0, MeOH).

IR (CHCl$_3$): 3426, 3031, 3012, 1717, 1502, 1340, 1230, 1228, 1045 cm$^{-1}$.

MS (FD): m/e 413 (M$^+$), 413 (100).

Analysis for C$_{22}$H$_{20}$NO$_3$SCl: Calcd: C, 63.84; H, 4.87; N, 3.38; Found: C, 64.12; H, 4.95; N, 3.54.

D. [3R-(3R*,4S*)]Benzyl 2-aza-3-(naphth-2-ylthiomethyl)-4-hydroxy-5-chloro pentanoate To a cold (0° C.) solution of 530 mg (1.28 mmol) of the subtitled intermediate of Preparation 1C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid.

Yield: 40%.

$^1$H NMR (CDCl$_3$): δ3.40 (s, 2H), 3.61–3.71 (m, 2H), 3.97–3.99 (m, 2H), 4.99 (s, 2H), 5.16 (br.s, 1H), 7.21–7.83 (complex, 12H).

MS (FD): m/e 415 (M$^+$), 415 (100).

[α]$_D$ −47.67° (c 0.86, MeOH).

IR (CHCl$_3$): 3630, 3412, 3011, 1720, 1502, 1236, 1044 cm$^{-1}$.

Analysis for C$_{22}$H$_{22}$NO$_3$ClS:

Calcd: C, 63.53; H, 5.33; N, 3.37;

Found: C, 63.72; H, 5.60; N, 3.64.

E. [3R-(3R*,4S*)]Benzyl 2-aza-3-oxiranyl-4-naphth-2-ylthio butanoate

A solution of 31 mg (0.55 mmol) of potassium hydroxide in 1 mL of ethanol was added to a solution of 190 mg (0.46 mmol) of the subtitled intermediate of Preparation 1D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid.

Yield: 99%.

$^1$H NMR (CDCl$_3$): δ2.76 (br.s, 2H) 3.01 (br.s, 1H), 3.31 (d, J=5 Hz, 2H), 3.77 (br.s, 1H), 5.05 (s, 2H), 5.22 (d, J=6 Hz, 1H), 7.25–7.85 (complex, 12H).

[α]$_D$ −125.42° (c 0.59, MeOH).

MS (FD): m/e 379 (M$^+$), 379 (100).

IR (CHCl$_3$): 3640, 3022, 2976, 1720, 1502, 1235, 1045 cm$^{-1}$.

Analysis for C$_{22}$H$_{21}$NO$_3$S: Calcd: C, 69.63; H, 5.58; N, 3.69; Found: C, 69.41; H, 5.53; N, 3.64.

F. [3R-(3R*,4R*,3'S*,4a'S*,8a'S*)]Benzyl, [2-aza-3-(naphth-2-ylthiomethyl)-4-hydroxy-5-(3'-(1"-N(t-butyl)amino-1"-oxomethyl)decahydroisoquinolin-2'-yl)]pentanoate A solution was prepared containing 165 mg (0.40 mmol) of the subtitled intermediate of Preparation 1E and 94 mg (0.43 mmol) of 3-(1-N(t-butyl)amino-1-oxomethyl)-decahydro-(2H)-isoquinoline in 5 mL of ethanol. The resulting reaction mixture was allowed to react at 80° C. for approximately 19 hours. The solution was then cooled to room temperature and concentrated under reduced pressure to provide a residue. This residue was purified using radial chromatography (eluent of 10% ethyl acetate in methylene chloride) to provide 103 mg of an off-white foam.

Yield: 42%.

$^1$H NMR (CDCl$_3$): δ1.10–1.73 (m, 20H), 2.13–2.31 (m, 2H), 2.44–2.53 (m, 1H), 2.56–2.68 (m, 1H), 2.86–2.97 (m, 1H), 3.52 (br.s, 2H), 4.02 (br.s, 2H), 4.98 (s, 2H), 5.65 (s, 1H), 5.94 (s, 1H), 7.25–7.83 (complex, 13H).

MS (FD): m/e 629 (M$^+$), 138 (100).

[α]$_D$ −92.45° (c 1.06, MeOH).

IR (CHCl$_3$): 3429, 3010, 2929, 1713, 1670, 1514, 1455, 1047 cm$^{-1}$.

Analysis for C$_{35}$H$_{47}$N$_3$O$_4$S: Calcd: C, 69.98; H, 7.67; N, 6.80; Found: C, 69.86; H, 7.78; N, 6.58.

G. [2R-(2R*,3R*,3'S*,4a'S*,8a'S*)]-N(t-butyl)-2'-[2-hydroxy-3-amino-4-(naphth-2-ylthio)]butyl decahydroisoquinoline-3'-carboxamide A solution was prepared containing 50 mg (0.081 mmol) of the subtitled intermediate of Preparation 1F and 1 mL of a 38% aqueous hydrobromic acid solution in acetic acid. The resultant reaction mixture was allowed to react at room temperature for approximately 1 hour and then was concentrated under reduced pressure to provide a residue. This residue was slurried with toluene and then concentrated under reduced pressure to provide 61 mg of the desired subtitled intermediate. This compound was used crude without purification in Example 9.

$^1$H NMR (CDCl$_3$): δ1.14 (s, 1H), 1.17–2.07 (complex, 15H), 2.66–2.87 (m, 2H), 3.21–3.25 (m, 2H), 3.75 (d, J=12

Hz, 1H), 3.85 (d, J=6 Hz, 1H), 4.36–4.47 (m, 1H), 6,73 (s, 1H), 7.39–7.90 (complex, 7H).

MS (FD): 483 (M+), 483 (100).

PREPARATION 2

A. (2R)-2-N(Benzyloxycarbonyl)amino-3-phenylthio prolanoic acid

The desired subtitled intermediate was prepared substantially in accordance with the procedure detailed in Procedure 1A, using 13.1 mL (127 mmol) of thiophenol, 4.6 g (117 mmol) of a 60% sodium hydride solution and 25.6 g (116 mmol) of (L)-N(benzyloxycarbonyl)serine β-lactone in 450 mL of tetrahydrofuran to provide a residue. This residue was purified using flash chromatography (gradient eluent of 0–2% acetic acid in a 4:1 methylene chloride/ethyl acetate mixture) to provide 27.9 g of a white solid.

Yield: 72%.

$^1$H NMR (CDCl$_3$): δ7.55–7.18 (m, 10H), 5.55 (d, J=7 Hz, 1H), 5.08 (s, 2H), 4.73–4.60 (m, 1H), 3.55–3.30 (m, 2H).

IR (KBr): 3304, 3035, 1687, 1532, 736 cm$^{-1}$.

MS (FD): m/e 332, 288, 271, 181.

Analysis for C$_{17}$H$_{17}$NO$_4$S: Calcd: C, 61.61; H, 5.17; N, 4.23; Found: C, 61.69; H, 5.22; N, 4.47.

B. (3R) Benzyl, 2-aza-3-phenylthiomethyl-4-oxo-5-diazo pentanoate

The desired subtitled compound was prepared substantially in accordance with the procedure detailed in Procedure 1B, using 12.1 g (37 mmol) of the subtitled compound of Preparation 2A, 5.09 mL (37 mmol) of triethylamine, 7.13 mL (55 mmol) isobutyl chloroformate, 146 mmol of a diazomethane solution to provide a residue. The diazomethane solution was prepared using 100 mL of diethylether, 150 mL of a 5N sodium hydroxide solution and 21 g (146 mmol) of N(methyl)-N(nitro)-N(nitroso)-guanidine as described in Preparation 1B. This residue was purified using flash chromatography (gradient eluent of 0–5% ethyl acetate in methylene chloride) to provide a yellow oil.

Yield: 73%.

$^1$H NMR (CDCl$_3$): δ7.50–7.19 (m, 10H), 5.62 (d, J=7 Hz, 1H), 5.47 (br.s, 1H), 5.11 (s, 2H), 4.50–4.32 (m, 1H), 3.33 (d, J=6 Hz, 1H).

IR (KBr): 3012, 2115, 1720, 1501, 1367, 1228 cm$^{-1}$.

MS (FD): m/e 356, 328, 242.

C. (3R) Benzyl, 2-aza-3-phenylthiomethyl-4-oxo-5-chloro pentanoate

The desired subtitled compound was prepared substantially in accordance with the procedure detailed in Procedure 1C, using 22.3 g (63 mmol) of the subtitled compound of Preparation 2B and small quantities of hydrochloric acid (gas) in 400 mL of diethylether to provide 21 g of a white solid. This solid was used without further purification.

$^1$H NMR (CDCl$_3$): δ7.50–7.15 (m, 10H), 5.56 (dd, J=2, 6.7 Hz, 1H), 5.11 (s, 2H), 4.78–4.67 (m, 1H), 4.20 (d, J=15.9 Hz, 1H), 4.12 (d, J=15.9 Hz, 1H), 3.48–3.23 (m, 2H).

IR (KBr): 3349, 1732, 1684, 1515, 1266 cm$^{-1}$.

MS (FD): m/e 363 (M+).

Analysis for C$_{18}$H$_{18}$NO$_3$SCl: Calcd: C, 59.42; H, 4.99; N, 3.85; Found: C, 59.57; H, 5.09; N, 4.13.

D. [3R-(3R*,4S*)]Benzyl, 2-aza-3-phenylthiomethyl-4-hydroxy-5-chloro pentanoate The subtitled compound was prepared substantially in accordance with the procedure detailed in Procedure 1D, using 21 g (58 mmol) of the subtitled compound of Preparation 2C, 2.4 g (63 mmol) of sodium borohydride in 300 mL of tetrahydrofuran to provide a residue. This residue was purified using flash chromatography (gradient eluent of 0–2% methanol in methylene chloride) followed by flash chromatography (gradient eluent of 0–2% ethyl acetate in chloroform) and then recrystallized from methylene chloride at −78° C. to provide 8.3 g of the desired subtitled compound.

Yield: 39%.

$^1$H NMR (CDCl$_3$): δ7.47–7.19 (m, 10H), 5.22–5.03 (m, 1H), 5.09 (s, 2H), 4.01–3.89 (m, 2H), 3.75–3.58 (m, 2H), 3.32 (d, J=4 Hz, 2H).

IR (KBr): 3321, 2951, 1688, 1542, 1246, 738 cm$^{-1}$.

MS (FD): m/e 366 (M+), 119.

Analysis for C$_{18}$H$_{20}$NO$_3$SCl: Calcd: C, 59.09; H, 5.51; N, 3.83; Found: C, 59.03; H, 5.50; N, 3.96.

E. [3R-(3R*,4S*)]Benzyl, 2-aza-3-oxiranyl-4-phenylthio butanoate

The desired subtitled compound was prepared substantially in accordance with the procedure detailed in Procedure 1E, using 8.3 g (23 mmol) of the subtitled compound of Preparation 2D, 1.4 g (25 mmol) of potassium hydroxide in 400 mL of ethanol to provide a residue. This residue was purified using flash chromatography (gradient eluent of 0–2% ethyl acetate in methylene chloride) to provide 6.4 g of a white solid.

Yield: 85%.

$^1$H NMR (CDCl$_3$): δ7.45–7.15 (m, 10H), 5.12 (S, 1H), 5.08 (s, 2H), 3.77–3.62 (m, 1H), 3.21 (d, J=6 Hz, 2H), 2.99 (m, 1H), 2.77 (m, 2H).

IR (KBr): 3303, 3067, 1694, 1538, 1257, 741 cm$^{-1}$.

MS (FD) m/e 329.

Analysis for C$_{32}$H$_{45}$N$_3$O$_4$S: Calcd: C, 65.63); H, 5.81; N, 4.25; Found: C, 65.48; H, 5.82; N, 4.29.

F. [3R-(3R*,4R*,3'S*,4a'S*,8a'S*)]Benzyl, [2-aza-3-phenylthiomethyl-4-hydroxy-5-(3'-(1"-N(t-butyl)amnino-1"-oxomethyl)decahydroisoquinolin-2'-yl) pentanoate The desired subtitled compound was prepared substantially in accordance with the procedure detailed in Procedure 1F, using 6.3 g (19 mmol) of the subtitled compound of Preparation 2E, 5 g (21 mmol) of 3-[N(t-butyl)aminocarbonyl]decahydro-(2H)-isoquinoline in 300 mL of ethanol to provide a residue. This residue was purified using flash chromatography (gradient eluent of 0–20% ethyl acetate in methylene chloride) to provide 4.3 g of a white solid.

Yield: 40%.

$^1$H NMR (CDCL$_3$): δ7.41–7.11 (m, 10H), 5.90 (d, J=5 Hz, 1H), 5.64 (s, 1H), 5.05 (d, J=4 Hz, 2H), 4.08–3.90 (m, 2H), 3.40 (d, J=6, 2H), 3.05 (s, 1H), 2.95–2.85 (m, 1H), 2.62–2.45 (m, 2H), 2.28–2.15 (m, 2H), 2.05–1.88 (m, 2H), 1.78–1.10 (m, 7H), 1.29 (s, 9H).

IR(KBr): 3330, 2925, 2862, 1706, 1661, 1520, 1454, 1246, 738, 694 cm$^{-1}$.

MS (FD): m/e 568 (M+), 467.

Analysis for C$_{32}$H$_{45}$N$_3$O$_4$S: Calcd: C, 67.69; H, 7.99; N. 7.40; Found: C, 67.64; H, 3.20; N, 7.45.

G. [2R-(2R*,3R*,3'S*,4a'S*,8a'S*)]-N(t-Butyl)-2'-[2-hydroxy-3-amino-4phenylthio]butyl decahydroisoquinoline-3'-carboxamide The desired subtitled compound was prepared substantially in accordance with the procedure detailed in Procedure 1G using 1 g (1.8 mmol) of the subtitled compound of Preparation 2F and 40 mL of a 30% hydrobromic acid in acetic acid solution, with the exception that the crude material was dissolved in 30 mL of methanol. To the resulting solution, was added 2 mL of diethylamine and 2 mL of concentrated ammonium hydroxide and then the mixture was concentrated under reduced pressure to provide a residue. This residue was redissolved in water and ethyl acetate. The resulting layers were separated and the organic layer was washed sequentially with an aqueous sodium bicarbonate solution and brine, dried over sodium sulfate, filtered and then reduced to dryness under reduced pressure to provide a residue. This residue was purified using flash chromatography (gradient eluent of 0–10% methanol in chloroform (containing 3 drops of ammonium hydroxide per 1000 mL of chloroform)) to provide 0.54 g of a white foam.

Yield: 71%.

$^1$H NMR (CDCl$_3$): δ7.41–7.16 (m, 5H), 6.07 (s, 1H), 3.78–3.70 (m, 1H), 3.45–3.38 (m, 1H), 3.03–2.84 (m, 3H), 2.38–2.20 (m, 3H), 2.00–1.05 (m, 12H), 1.33 (s, 9H).

IR (KBr): 2924, 2862, 1660, 1517, 1454, 1439, 737, 691 cm$^{-1}$.

MS (FD): m/e 434 (M$^+$), 293.

PREPARATION 3

A. [3S-(3R*,4aR*,8aR*,2'S*,3'R*)]-2-[3-N(Benzyloxycarbonyl)amino-2'-hydroxy-4'-phenyl]butyl-N(t-butyl)decahydroisoquinoline-3-carboxamide A solution of [1R-(1R*,3S*,1'S*,4aS*,8aS*)]-1-[(1'-N-benzyloxycarbonylamino-2'-phenyl)ethyl]oxirane and decahydroisoquinoline-3-N-t-butylcarboxamide in absolute ethanol was heated at 80° C. overnight. The reaction mixture was reduced to dryness under reduced pressure to provide a residue. This residue was purified using flash chromatography (gradient eluent of 10–50% ethyl acetate in methylene chloride) to provide 6.47 g of an off-white foam.

Yield: 75%.

$^1$H NMR (CDCl$_3$): δ1.29 (s, 9H), 1.25–2.05 (m, 2H), 2.20–2.35 (m, 2H), 2.55–2.70 (m, 11H), 2.85–3.10 (m, 3H), 3.24 (br.s, 1H), 3.82 (br.s, 1H), 3.98 (br.s, 1H), 4.99 (br.s, 2H), 5.16–5.18 (m, 1H), 5.80 (br.s, 1H), 7.05–7.38 (m, 10H).

IR (CDCl$_3$): 3600–3100 (br.), 3031, 2929, 1714, 1673, 1512, 1455, 1368, 1232, 1199, 1047 cm$^{-1}$.

MS (FD): m/e 536 (M$^+$H), 1068 (100).

B. [3S-(3R*,4aR*,8aR*,2'S*,3'R*)]-2-[3'-Amino-2-hydroxy-4'-phenyl]butyl-decahydroisoquinoline-3-N-t-butylcarboxamide A rapidly stirring suspension of 6.37 g (11.91 mmol) of the subtitled intermediate of Preparation 3A and 1.2 g of 10% palladium-on-carbon in 200 mL of absolute ethanol was placed under an atmosphere of hydrogen. After approximately 48 hours, the reaction mixture was filtered through celite. The resultant filtrate was then reduced to dryness under reduced pressure to provide 5.09 g of the desired subtitled intermediate.

$^1$H NMR (CDCl$_3$): δ1.33 (s, 9H), 1.40–1.95 (m, 10H), 2.25–2.48 (m, 2H), 2.59–2.75 (m, 3H), 2.80–3.40 (m, 7H), 3.75–3.90 (m, 1H), 6.19 (br.s, 1H), 7.18–7.35 (m, 5H).

IR (CDCl$_3$): 3600–3100 (br. 2929, 2865, 1671, 1515, 1455, 1367, 1245, 1047 cm$^{-1}$.

MS (FD) m/e 402 (M$^+$, 100).

PREPARATION 4

A. 2R-N(Benzyloxycarbonyl)amino-3-naphth-2-ylthio propanoic acid

To a solution of 1.28 g (8.00 mmol) of naphthalene-2-thiol in 30 mL of tetrahydrofuran, was slowly added 1.77 g (8.16 g) of 60% sodium hydride, under nitrogen. After stirring for approximately 15 minutes, a solution of N(benzyloxycarbonyl)serine-β-lactone in 20 mL of tetrahydrofuran was slowly added. The reaction mixture was allowed to react at room temperature for approximately one hour, and then was concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid.

Yield: 68%.

$^1$H NMR (CDCl$_3$): δ3.42–3.61 (br.m, 2H), 5.53–5.76 (br.s, 1H), 4.85–5.08 (br.m, 2H), 5.54–5.76 (br.s, 1H), 7.06–7.97 (m, 12H).

[α]$_D$ –55.72° (c 1.0, MeOH).

IR (KBr): 3348, 3048, 1746, 1715, 1674, 1560, 1550, 1269, 1200, 1060 cm$^{-1}$.

MS(FD): m/e 381 (M$^+$), 381 (100).

Analysis for C$_{20}$H$_{19}$NO$_4$S: Calcd: C, 66.12; H, 5.02; N, 3.67; Found: C, 66.22; H, 5.04; N, 3.86.

B. 3R-1-Diazo-2-oxo-3-N-(benzyloxycarbonyl)amino-4-(naphth-2-ylthio) butane

To a cold (–30° C.) solution of 15.38 g (40.3 mmol) of the subtitled compound of Preparation 4A in 230 mL of ethyl acetate, was slowly added 5.62 mL (40.3 mmol) of triethylamine, under nitrogen via syringe. To the resulting solution was then added 7.84 mL (60.5 mmol) of isobutyl chloroformate, via syringe. In a separate flask, 10 g of N(methyl)-N(nitro)-N(nitroso)-guanidine was carefully added to a bilayer mixture of 170 mL of diethylether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethylether and sodium hydroxide and 30 g of N(methyl)-N(nitro)-N(nitroso)-guanidine. The resultant diazomethane reactant was then added to the mixed anhydride solution prepared above and the reaction mixture was allowed to react cold (–30° C.) for approximately 20 minutes. When the reaction was substantially complete, as indicated by TLC, nitrogen was bubbled through the solution using a fire polished Pasteur pipet to remove any excess diazomethane and then the solution was concentrated under reduced pressure to provide a residue. This residue was purified using flash chromatography (eluent of 10% ethyl acetate in methylene chloride) to provide 13.62 g of a yellow oil.

Yield: 83%.

$^1$H NMR (CDCl$_3$): δ3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. 3R-1-Chloro-2-oxo-3-N-(benzyloxycarbonyl)amino-4-(naphth-2-ylthio) butane

A short burst (about 2 seconds) of anhydrous hydrochloric acid (gas) was passed through a cold (–20° C.) solution of 13.62 g (33.59 mmol) of the subtitled compound of Preparation 4B in 230 mL of diethylether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid.

Yield: 87%.

$^1$H NMR (CDCl$_3$): δ3.41 (dd, J=12, 6 Hz, 1H), 3.53 (dd, J=12,6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (m, 12H).

$[\alpha]_D$ –80.00° (c 1.0, MeOH).

IR (CHCl$_3$): 3426, 3031, 3012, 1717, 1502, 1340, 1230, 1228, 1045 cm$^{-1}$.

MS(FD): m/e 413 (M$^+$), 413 (100).

Analysis for C$_{22}$H$_{20}$NO$_3$SCl: Calcd: C, 63.84; H, 4.87; N, 3.38; Found: C, 64.12; H, 4.95; N, 3.54.

D. [3R-(3R*,4S*)]-1-Chloro-2-hydroxy-3-N-(benzyloxycarbonyl)amino-4-(naphth-2-ylthio)butane To a cold (0° C.) solution of 530 mg (1.28 mmol) of the subtitled compound of Preparation 4C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid.

Yield: 40%.

$^1$H NMR (CDCl$_3$): δ3.40 (s, 2H), 3.61–3.71 (m, 2H), 3.97–3.99 (m, 2H), 4.99 (s, 2H), 5.16 (br.s, 1H), 7.21–7.83 (complex, 12H).

MS(FD): m/e 415 (M$^+$), 415 (100).

$[\alpha]_D$ –47.67° (c 0.86, MeOH).

IR (CDCl$_3$): 3630, 3412, 3011, 1720, 1502, 1236, 1044 cm$^{-1}$.

Analysis for C$_{22}$H$_{22}$NO$_3$ClS: Calcd: C, 63.53; H, 5.33; N, 3.37; Found: C, 63.72; H, 5.60; N, 3.64.

E. 1'R-(1'R*,1S*)]-1-[(1'-N-(Benzyloxycarbonyl)amino-2'-(naphth-2-ylthio)ethyl]oxirane A solution of 31 mg (0.55 mmol) of potassium hydroxide in 1 mL of ethanol was added to a solution of 190 mg (0.46 mmol) of the subtitled compound of Preparation 4D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid.

Yield: 99%.

$^1$H NMR (CDCl$_3$): δ2.76 (br.s, 2H) 3.01 (br.s, 1H), 3.31 (d, J=5 Hz, 2H), 3.77 (br.s, 1H), 5.05 (s, 2H), 5.22 (d, J=6 Hz, 1H), 7.25–7.85 (complex, 12H).

$[\alpha]_D$ –125.42° (c 0.59, 14eOH)

MS(FD): m/e 379 (M$^+$), 379 (100).

IR (CHCl$_3$): 3640, 3022, 2976, 1720, 1502, 1235, 1045 cm$^{-1}$.

Analysis for C$_{22}$H$_{21}$NO$_3$S: Calcd: C, 69.63; H, 5.58; N, 3.69; Found: C. 69.41; H, 5.53; N, 3.64.

F. [2S-(2R*,2'R*,3'S*)]-1-[2'-Hydroxy-3'-(N-benzyloxycarbonyl)amino-4'-(naphth-2-ylthio)butyl]piperidine-2-N-(t-butyl)carboxamide A solution of 0.51 g (1.34 mmol) of the subtitled compound of Preparation 4E and 0.26 g (1.41 mmol) of the subtitled compound of Preparation 6C in 25 mL of isopropanol was heated to 55° C. for approximately forty eight hours. The resultant reaction mixture was cooled and then concentrated under reduced pressure to provide a crude material. This material was purified using radial chromatography (4mm plate; eluent of 10% acetone in methylene chloride) to provide 104 mg of a white foam.

Yield: 14%.

$^1$H NMR (CDCl$_3$): δ1.29 (s, 9H), 1.44–1.82 (m, 6H), 2.19 (m, !H), 2.40 (m, 1H), 2.68 (m, 2H), 3.09 (m, 1H), 3.46 (m, 2H), 4.00 (m, 2H), 5.01 (s, 2H), 5.73 (d, 1H), 6.01 (br.s, 1H), 7.23–7.34 (m, 5H), 7.45 (m, 3H), 7.72–7.83 (m, 4H).

MS(FD): m/e 563 (M$^+$, 100).

G. [2S-(2R*,2'S*,3'S*)]-1-[2'-Hydroxy-3'-amino-4'-naphth-2-ylthio)butyl]piperidine-2-N-(t-butyl)carboxamide A solution containing 1.05 g (0.18 mmol) of the subtitled compound of Preparation 4F in 10 mL of 30% hydrobromic acid in acetic acid was reacted for approximately one hour. The resultant reaction mixture was concentrated, azeotroped three times with toluene, redissolved in methanol containing 4.5 mL each of diethylamine and ammonium hydroxide and then concentrated under reduced pressure to provide a residue. This residue was purified using radial chromatography (1 mm plate; eluent of 3% methanol in methylene chloride containing 1% acetic acid) to provide 64 mg a white foam.

Yield: 80%.

$^1$H NMR (CDCl$_3$): δ1.29 (s, 9H), 1.52–1.73 (m, 6H), 1.84 (m, 1H), 2.31–2.43 (m, 2H), 2.75–3.04 (m, 5H), 3.17 (m, 1H), 3.41 (m, 1H), 3.71 (m, 1H), 6.22 (br.s, 1H), 7.47 (m, 3H), 7.73–7.82 (m, 4H).

MS(FD): m/e 430 (M$^+$, 100).

PREPARATION 5

A. 2S-N-(Benzyloxycarbonyl)-2-pyrrolidinecarboxylate pentafluorophenyl ester To a cold (0° C.) solution of 30 g (0.12 mol) of 2S-N (benzyloxycarbonyl)-2-pyrolidinecarboxylic acid and 25.8 g (0.14 mol) of pentafluorophenol in 450 mL of tetrahydrofuran, was added 27.7 g (0.14 mol) of 1-(3-dimethylaminopropyl)-3-ethylcarbodiimide (EDC) in one portion, followed by 150 mL of methylene chloride. The resultant reaction mixture was warmed to room temperature and reacted for approximately four hours. When the reaction was substantially complete, as indicated by TLC, the reaction mixture was concentrated under reduced pressure to provide a residue. This residue was dissolved in 500 mL of ethyl acetate and washed sequentially with water, potassium carbonate, 1N hydrochloric acid and brine, dried over sodium sulfate, filtered and then reduced to dryness under reduced pressure to provide a solid. This solid was redissolved in hexane and washed with potassium carbonate, dried over sodium sulfate, filtered and reduced to dryness under reduced pressure to provide 45.95 g of the desired subtitled compound.

Yield: 92%.

$^1$H NMR (CDCl$_3$): δ1.95–2.15 (m, 2H), 2.20–2.35 (m, 1H), 2.35–2.50 (m, 1H), 3.50–3.75 (m, 2H), 4.65–4.75 (m, 1H), 5.02–5.30 (m, 2H), 7.20–7.45 (m, 5H).

B. 2S-N-(Benzyloxycarbonyl)pyrrolidine-2-N(t-butyl)carboxamide

To a cold (0° C.) solution of 45.90 g (0.111 mmol) of the subtitled compound of Preparation 5A in 100 mL of anhydrous methylene chloride, was slowly added 100 mL (0.952 mmol) of t-butylamine. The reaction mixture was warmed to room temperature and reacted for approximately one hour and then diluted with 1000 mL of methylene chloride and then washed sequentially with 1N potassium carbonate, 1N hydrochloric acid, 1N potassium carbonate, and brine, dried over sodium sulfate, and then plug filtered using 50% ethyl acetate in hexane to provide 37.74 g of the desired compound which was used without further purification.

$^1$H NMR (CDCl$_3$): δ0.95–1.50 (m, 9H), 1.70–2.40 (m, 4H), 3.30–3.60 (m, 2H), 4.10–4.30 (m, 1H), 4.95–5.35 (m, 2H), 5.65 (br.s, 0.5H), 6.55 (br.s, 1H), 7.20–7.50 (m, 5.5H).

C. 2S-Pyrrolidine-2-N-(t-Butyl)carboxamide

A rapidly stirring suspension of 2.71 g (8.9 mmol) of the subtitled compound of Preparation 5B and 500 mg of 10% palladium-on-carbon in 200 mL of ethanol was placed under an atmosphere of hydrogen. After approximately 48 hours, the reaction mixture was filtered through celite and reduced to dryness under reduced pressure to provide 1.53 g of the desired subtitled compound. This compound was used without further purification.

Yield: 100%.

$^1$H NMR (CDCl$_3$): δ1.35 (s, 9H), 1.60–1.75 (m, 2H), 1.76–1.90 (m, 1H), 2.00–2.15 (m, 1H), 2.58 (br.s, 1H), 2.80–3.05 (m, 2H), 3.55–3.65 (m, 1H), 7.45 (br.s, 1H).

D. [2S-(2R*,2'S*,3'R*)]-1-[3'-N(Benzyloxycarbonyl)amino-2'-hydroxy-4'-phenylbutyl]pyrrolidine-2-N-(t-butyl)carboxamide A solution containing 122 mg (0.72 mmol) of the subtitled compound of Preparation 5C and 200 mg (0.68 mmol) of [1S-(1R*,1'R*)]-1-[(1'-N-(benzyloxycarbonyl)amino-2'-phenyl)ethyl]oxirane in 10 mL of methanol was stirred overnight. When the reaction was substantially complete, as indicated by TLC, the reaction mixture was concentrated under reduced pressure. The desired compound was purified using column chromatography (gradient eluent of 2–4% methanol in methylene chloride) to provide 232.2 mg of a clear amorphous solid.

Yield: 55%.

[α]$_D$ −56.97° (c=0.27, MeOH).

$^1$H NMR (CDCl$_3$): δ1.33 (s, 9H), 1.55–1.95 (m, 4H), 2.05–2.25 (m, 1H), 2.40–2.55 (m, 1H), 2.65–2.75 (m, 2H), 2.80–3.00 (m, 3H), 3.15–3.30 (m, 1H), 3.65–3.75 (m, 1H), 3.85–3.95 (m, 1H), 4.86 (br.d, J=1.1 Hz, 1H), 5.03 (s, 2H), 6.95 (m, 1H), 7.15–7.40 (m, 10H).

IR (CHCl$_3$): 3700–3100 (br.), 3434, 3031, 2976, 1720, 1664, 1604, 1512, 1455, 1394, 1367, 1343, 1233, 1156, 1107, 1063, 1028, 911 cm$^{-1}$.

MS(FD): m/e 468 (M$^+$, 100).

E. [2S-(2R*,2'S*,3'R*)]-1-[3'-Amino-2'-hydroxy-4'-phenylbutyl] pyrrolidine-2-N-t-butylcarboxamide The subtitled compound of Preparation 5D (222 mg, 0.47 mmol) was deprotected substantially as detailed in Preparation 5C, using 67 mg of 10% palladium-on-carbon and hydrogen gas (1 atmosphere) in 15 mL of ethanol. The desired compound was purified using column chromatography (eluent of 10% isopropanol in methylene chloride containing 0.75% ammonium hydroxide) to provide 80 mg of an off-white solid.

Yield: 51%.

[α]$_D$ −55.26° (c=0.23, MeOH).

$^1$H NMR (CDCl$_3$): δ0.80–3.70 (m, 25H), 6.90–7.40 (m, 6H).

IR (CHCl$_3$): 3692, 3600–3200 (br.), 2975, 1657, 1603, 1522, 1497, 1479, 1455, 1393, 1366, 1232, 1198, 1137, 1049, 882 cm$^{-1}$.

MS(FD): m/e 334 (M$^+$, 100).

PREPARATION 6

A. 2S-N-(t-Butoxycarbonyl) piperidine-2-carboxylic acid

A solution of 1.64 g of sodium carbonate in 15 ml of water was added to a cold (0° C.) solution of 2.0 g (15.5 mol) of 2S-piperidinecarboxylic acid in 50 mL of dioxane. After approximately ten minutes, 3.7 g (17.0 mol) of di-t-butyl dicarbonate was added to the mixture. The resultant reaction mixture was reacted for approximately six hours, concentrated to one fourth of the original volume and then acidified to pH 2 using 1M sodiumhydrogen sulfate and ethyl acetate. The resulting layers were separated, and the organic layers were washed with a saturated brine solution, dried over sodium sulfate, filtered and then reduced to dryness under reduced pressure to provide 2.67 g of a white crystalline solid.

Yield: 75%.

[α]$_D$ −55.26° (c=0.23, MeOH)

$^1$H NMR (CDCl$_3$): δ1.20–1.80 (m, 15H), 2.15–2.30 (m, 1H), 2.85–3.10 (m, 1H), 3.90–4.10 (m, 2H), 4.70–5.00 (m, 1H).

IR (CHCl$_3$): 3700–1800 (br.), 3025, 3018, 3011, 2980, 2947, 2865, 1716, 1685, 1449, 1394, 1368, 1280, 1252, 1162, 1147, 1129 cm$^{-1}$.

MS(FD): m/e 229 (M$^+$, 100).

Analysis for $C_{27}H_{37}N_3O_4$: Calcd: C, 57.63; H, 8.35; N, 6.11; Found: C, 57.90; H, 8.35; N, 6.19.

B. 2S-N-(t-Butoxycarbonyl) piperidine-2-carboxylate. pentafluorophenylester

To a cold (0° C.) solution of 2.53 g (11.03 mol) of the subtitled compound of Preparation 6A and 2.34 g (12.7 mol) of pentafluorobenzoic acid in 50 mL of tetrahydrofuran, was added 2.42 g (12.7 mol) of EDC. The resultant reaction mixture was warmed to room temperature and reacted for approximately two hours. The mixture was then concentrated under reduced pressure to provide a solid. This solid was redissolved in methylene chloride and washed sequentially with potassium carbonate and brine, dried over sodium sulfate, filtered and then reduced to dryness under reduced pressure to provide 3.85 g of a clear oil which solidified on standing.

Yield: 88%.

$^1$H NMR (CDCl$_3$): δ1.20–1.90 (m, 15H), 2.30–2.40 (m, 1H), 2.90–3.15 (m, 1H), 3.90–4.15 (m, 1H), 5.05–5.35 (m, 1H).

C. 2S-N-(t-Butoxycarbonyl) piperidine-2-N-t-butylcarboxamide

To a cold (0° C.) solution of 3.8 g (9.6 mmol) of the subtitled compound of Preparation 6B in 200 mL of methylene chloride, was slowly added 2.53 mL (24.0 mmol) of t-butylamine. The reaction mixture was reacted for approximately four hours and then concentrated under reduced pressure to provide a residue. This residue was redissolved in methylene chloride and then washed sequentially with 1M potassium carbonate and brine, dried over sodium sulfate, filtered and then purified using column chromatography (gradient eluent of 10–20% ethyl acetate in hexane) to provide 2.52 g of a white solid.

Yield: 92%.

$[α]_D$ −41.47° (c=0.506, MeOH).

$^1$H NMR (CDCl$_3$): δ1.10–1.70 (m, 15H), 2.20–2.35 (m, 1H), 2.65–2.82 (m, 1H), 3.90–4.10 (m, 1H), 4.62 (br.s, 1H).

IR (CHCl$_3$): 3600–3300 (br.), 2978, 2945, 2869, 1677, 1512, 1455, 1413, 1394, 1367, 1317, 1280, 1255, 1162, 1144, 1127, 1078, 1042, 868 cm$^{-1}$.

MS(FD): m/e 284 (M$^+$, 100).

Analysis for C$_{15}$H$_{28}$N$_2$O$_3$: Calcd: C, 63.35; H, 9.92; N, 9.85; Found: C, 63.10; H, 9.66; N, 9.92.

D. 2S-Piperidine-2-N-t-butylcarboxamide

A solution containing 1.0 g (3.5 mol) of the subtitled compound of Preparation 6C and 3.5 mL of trifluoroacetic acid in 25 mL of methylene chloride was stirred at room temperature for approximately two hours. The reaction mixture was concentrated and azeotroped once with toluene. The resultant reaction mixture was then partitioned between methylene chloride and sodium bicarbonate. The resulting layers were separated and organic layer was dried over sodium sulfate, filtered and reduced to dryness under reduced pressure to provide 641 mg of the subtitled compound.

Yield: 99%.

$[α]_D$ −22.45° (c=0.95, MeOH)

$^1$H NMR (CDCl$_3$): δ1.20–1.50 (m, 12H), 1.51–1.62 (m, 1H), 1.64 (s, 1H), 1.75–1.88 (m, 1H), 1.90–2.00 (m, 1H), 2.60–2.72 (m, 1H), 2.98–3.10 (m, 2H), 6.63 (br.s, 1H).

IR (CHCl$_3$): 3363, 3002, 2969, 2940, 2860, 1738, 1660, 1522, 1480, 1455, 1398, 1367, 1324, 1295, 1230, 1129, 1110, 852 cm$^{-1}$.

MS(FD): m/e 184 (M$^+$, 100).

E. [2S-(2R*,2'S*,3'R*)]-N-[3'-(N-Benzyloxycarbonyl)amino-2'-hydroxy-4'-phenyl]butyl piperidine-2-N-t-butylcarboxamide A solution containing 195 mg (1.06 mmol) of the subtitled compound of Preparation 6D and 300 mg (1.01 mmol) of (1S-(1R*,1'R*)]-1-[(1'-N(benzyloxycarbonyl)amino-2'-phenyl)ethyl]oxirane in 10 mL of isopropanol was stirred at 55° C. for approximately forty eight hours. When the reaction was substantially complete, as indicated by TLC, the reaction mixture was concentrated under reduced pressure. The desired compound was purified using column chromatography (gradient eluent of 1–5% isopropanol in methylene chloride).

Yield: 395 mg (81%).

$[α]_D$ −55.64° (c=0.22, MeOH)

$^1$H NMR (CDCl$_3$): δ1.32 (s, 9H), 1.45–1.90 (m, 6H), 2.25–2.50 (m, 2H), 2.70–3.20 (m, 5H), 3.30–3.40 (m, 1H), 3.75–4.05 (m, 2H), 4.95–5.10 (m, 3H), 6.15 (br.s, 1H), 7.18–7.40 (m, 10H).

IR (CHCl$_3$): 3700–3100 (br.), 3623, 3021, 2976, 1668, 1603, 1511, 1456, 1313, 1047, 878 cm$^{-1}$.

MS(FD): m/e 482 (M$^+$, 100).

F. [2S-(2R*,2'S*,3'R*)]-N-[3'-Amino-2'-hydroxy-4'-phenyl]butyl piperidine-2-N-t-butylcarboxamide The subtitled compound of Preparation 6E (371 mg, 0.77 mmol) was deprotected substantially as detailed in Preparation 5C, using 110 mg of 10% palladium-on-carbon and hydrogen gas in 20 mL of ethanol to provide 260 mg of a white foam.

Yield: 97%.

$[α]_D$ −4.92° (c=0.39, MeOH)

$^1$H NMR (CDCl$_3$): δ1.35 (s, 9H), 1.45–1.90 (m, 6H), 2.25–2.35 (m, 1H), 2.50–2.90 (m, 5H), 3.00–3.40 (m, 3H), 3.85–3.98 (m, 1H), 6.29 (s, 1H), 7.15–7.38 (m, 5H).

IR (CHCl$_3$): 3693, 3650–3100 (br.), 2943, 2862, 1671, 1603, 1517, 1497, 1455, 1394, 1367, 1233, 1185, 1049, 887 cm$^{-1}$.

MS(FD): m/e 348 (M$^+$, 100).

PREPARATION 7

A. Pyrazine-2-N-(t-butyl)carboxamide

To a slurry of 50 g (0.403 mol) pyrazine-2-carboxylic acid in 600 mL of tetrahydrofuran and 100 mL of dimethylformamide, was added 65.9 g (0.407 mol) of carbonyldiimidazole. The resultant reaction mixture was reacted at 50° C. until gas evolution ceased. After the reaction mixture cooled, 73.5 g (1.00 mol) of t-butylamine was slowly added. The reaction mixture was reacted for approximately thirty minutes, concentrated under reduced pressure, redissolved in 500 mL of methylene chloride and then washed sequentially with water, hydrochloric acid (pH 2), saturated sodium bicarbonate, water, 1M potassium hydroxide, and brine, dried over sodium sulfate, and concentrated to provide 68.5 g of a white solid.

Yield: 95%.

$^1$H NMR (CDCl$_3$): δ1.51 (s, 9H), 7.73 (br.s, 1H), 8.49 (m, 1H), 8.72 (m, 1H), 9.38 (s, 1H).

B. (±)-Piperazine-2-N-(t-butyl)carboxamide

A mixture of 68.5 g (0.382 mol) of the subtitled compound of Preparation 7A, 70 g (0.308mol) of platinum oxide in 186 mL of ethanol was heated overnight at 40° C. under a hydrogen atmosphere (60 psi). The resultant crude material was filtered and the filtrate was concentrated to provide 65 g of white solid.

Yield: 95%.

MS(FD): m/e 185 (M$^+$, 100).

C. (±)-4-(Pyrid-3'-ylmethyl)piperazine-2-N-(t-butyl) carboxamide

To a solution of 5.0 g (0.027 mol) of the subtitled compound of Preparation 7B in 160 mL of a 1:1 mixture of water and acetonitrile, was added 18.65 g (0.135 mol) of potassium carbonate. The resultant mixture was vigorously stirred during the addition of 4.43 g (0.027 mol) of 3-chloromethylpyridine hydrochloride and then allowed to react overnight. The resultant reaction mixture was concentrated under reduced pressure, slurried in a solution of 20% isopropanol in chloroform and washed sequentially with water and brine, dried over sodium sulfate, filtered and then concentrated to provide a residue. This residue was purified using flash chromatography (eluent of 5% methanol in methylene chloride containing 1% ammonium hydroxide) to provide 1.34 g of a clear yellow oil.

Yield: 18%.

$^1$H NMR (CDCl$_3$): δ1.10 (s, 9H), 1.39–2.01 (m, 2H), 2.35 (m, 1H), 2.57–2.74 (m, 4H), 3.09 (m, 1H), 3.27 (s, 2H), 6.71 (br.s, 1H), 7.03 (m, 1H), 7.44 (m, 1H) 8.26 (m, 2H).

IR (KBr): 3691, 3611, 3366, 2974, 1666, 1602, 1521, 1479, 1456, 1427, 1393, 1366, 1324, 1139, 1047, 839 cm$^{-1}$.

MS(FD): m/e 276 (M$^+$, 100).

D. [2S-(2R*,2'S*,3'R*)]-1-[2'-Hydroxy-3'-(N-benzyloxycarbonyl)amino-4'-phenylbutyl]-4-(pyrid-3"-ylmethyl) piperazine-2-N-(t-butyl)carboxamide A solution containing 0.377 g (1.27 mmol) of [1S-(1R*,1'R*)]-1-[(1'-N-Benzyloxycarbonyl)amino-2-phenyl)ethyl] oxirane and 0.350 g (1.27 mmol) of the subtitled compound of Preparation 7C in 12 mL of isopropanol was reacted at 45° C. for approximately forty eight hours. The reaction mixture was cooled and then concentrated under reduced pressure to provide a crude material. This material was purified using radial chromatography (6mm plate; gradient eluent of 5–10% isopropanol in methylene chloride) to provide 120 mg of isomer A and 68 mg of isomer B.

Yield: 26% overall.

Isomer A $^1$H NMR (CDCl$_3$): δ1.33 (S, 9H), 2.26–2.89 (m, 13H) 3.29 (m, 1H), 3.45 (s, 2H), 3.79–3.95 (m, 3H), 4.73 (br.s, 1H), 4.97 (br.s, 2H), 5.20 (m, 1H), 7.14–7.29 (m, 6H) 7.57 (m, 1H), 7.82 (br.s, 1H), 8.53 (m, 2H).

IR (KBr): 3692, 3434, 2970, 2829, 1714, 1661, 1604, 1579, 1512, 1455, 1427, 1393, 1365, 1231, 1149, 1029, 909 cm$^{-1}$.

MS(FD): m/e 573 (M$^+$, 100).

E. [2S-(2R*,2'S*,3'R*)]-1-[2'-Hydroxy-3'-amino-4'-phenyl]butyl-4-(pyrid-3"-ylmethyl) piperazine-2-N-(t-butyl)carboxamide A solution containing 0.062 g (0.11 mmol) of the subtitled compound of Preparation 7D (isomer A) was stirred for approximately ninety minutes in 1.5 mL of a solution of 30% hydrobromic acid in acetic acid. The resultant mixture was concentrated, azeotroped three times with toluene, redissolved in methanol containing 1 mL each of diethylamine and ammonium hydroxide and then concentrated under reduced pressure to provide a residue. This residue was purified using radial chromatography (2 mm plate; gradient eluent of 15–25% methanol in methylene chloride containing 1% ammonium hydroxide) to provide 13 mg of a white solid.

Yield: 28%.

$^1$H NMR (CDCl$_3$): δ1.33 (s, 9H), 2.36–3.21 (m, 15H), 3.47 (d, 2H), 3.75 (m, 1H), 7.19–7.30 (m, 6H) 7.57 (m, 2H), 8.52 (m, 2H).

MS(FD): m/e 440 (M$^+$, 100).

PREPARATION 8

A. [2S-(2R*,2'S*,3'S*)]-1-[3'-N-(Benzyloxycarbonyl)amino-2'-hydroxy-4'-phenylthiobutyl]-4-[pyrid-3"-ylmethyl] piperazine-2-N-t-butylcarboxamide [isomer B]

A solution of 596 mg (1.81 mmol) of [1S-(1R*,1'S*)]-1-[1'-N-(benzyloxycarbonyl)amino-2'-(phenylthio)ethyl] oxirane and 500 mg (1.81 mmol) of the subtitled compound of Preparation 7C in 15 mL of isopropanol were heated at 43° C. for approximately forty-eight hours. The reaction was monitored using TLC (10% isopropanol in methylene chloride containing 1% ammonium hydroxide; Isomer A R$_f$=0.7; Isomer B R$_f$=0.6). When the reaction was substantially complete, the reaction mixture was concentrated under reduced pressure to provide a residue. This residue was purified using radial chromatography (6 mm plate; gradient eluent of 5–15% isopropanol in methylene chloride containing 1% ammonium hydroxide) to provide 200 mg of isomer A as a light tan foam and 119 mg of an off-white foam (isomer B).

Isomer A

Yield: 18%.

$^1$H NMR (CDCl$_3$): δ1.31 (s, 9H), 2.25–2.62 (m, 7H), 2.78–2.95 (m, 2H), 2.98–3.08 (m, 1H), 3.10–3.25 (m, 2H), 3.40–3.55 (m, 2H), 3.72–3.85 (m, 1H), 3.90–4.00 (m, 1H), 5.05 (s, 2H), 7.01 (br.s, 1H), 7.10–7.40 (m, 11H), 7.62 (d, J=7.8 Hz, 1H), 8.49 (s, 2H).

MS(FD): m/e 606 (M$^+$, 100).

Analysis for C$_{33}$H$_{43}$N$_5$O$_4$S: Calcd: C, 65.42; H, 7.15; N, 11.56; Found: C, 65.38; H, 7.27; N, 11.36.

Isomer B

Yield: 11%.

$^1$H NMR (CDCl$_3$): δ1.33 (s, 9H), 2.25–2.85 (m, 8H), 3.20–3.32 (m, 3H), 3.47 (s, 2H), 3.78–3.95 (m, 2H), 5.06 (s, 2H), 5.30–5.38 (m, 1H), 7.10–7.42 (m, 12H), 7.55–7.85 (m, 2H), 3.50–8.60 (m, 2H).

MS (FD): m/e 606 (M), 497 (100).

HR MS(FAB) for C$_{33}$H$_{44}$N$_5$O$_4$S: Calcd: 606.3114; Found: 606.3141.

B. [2S-(2R*,2'S*,3'S*)]-1-[2'-Hydroxy-3'-amino-4'-phenylthiobutyl]-4-[pyrid-3"-ylmethyl] piperazine-2-N-t-butylcarboxamide A solution of 110 mg (0.18 mmol) of isomer B from Preparation 8A in 5 mL of 30% hydrobromic acid in acetic acid was stirred at room temperature for approximately 1 hour. The reaction mixture was concentrated under reduced pressure to provide a residue. This residue was redissolved in 4 mL of ammonium hydroxide. The resultant solution was extracted four times with 10 mL portions of a 10% solution of isopropanol in chloroform. The combined organic layers were dried over sodium sulfate, filtered and concentrated under reduced pressure to provide a residue. This residue was purified using radial chromatograghy (2 mm plate; gradient eluent of 10–30% methanol in methylene chloride containing 1% ammonium hydroxide) to provide 65 mg of a light yellow foam.

Yield: 72%.

$^1$H NMR (CDCl$_3$): δ1.25 (s, 9H), 2.25–2.73 (m, 7H), 3.00–3.32 (m, 4H), 3.47 (s, 2H), 3.60–3.75 (m, 1H), 4.18–4.35 (m, 1H), 6.90–7.65 (m, 9H), 8.40–8.60 (m, 2H).

MS(FD): m/e 473 (M$^+$, 100).

EXAMPLE 1

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(t-butoxycarbonyl)amino-8-benzyloxy] octyl decahydroisoquinoline-3"-carboxamide The titled compound is prepared by adding dicyclohexylcarbodiimide (DCC) to a cold (0° C.) solution containing the subtitled intermediate of Preparation 1G, hydroxybenzotriazole hydrate (HOBT.H₂O) and (2R)-2-N(t-butoxycarbonyl)amino-4-oxo-4-benzyloxy butanoic acid in a tetrahydrofuran/dimethylformamide solution, under nitrogen. After allowing the resulting reaction mixture to slowly warm to room temperature and react for from 1–24 hours, the desired compound is isolated using standard techniques and then further purified, if necessary using flash chromatography.

EXAMPLE 2

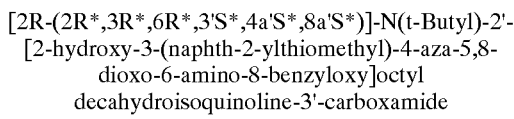

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-amino-8-benzyloxy]octyl decahydroisoquinoline-3'-carboxamide The titled compound is prepared by adding trifluoroacetic acid to a cold (0° C.) solution of the titled compound of Example 1 and triethylsilane in methylene chloride. After allowing the resulting reaction mixture to react for approximately thirty minutes at 0° C., the reaction mixture is warmed to room temperature and allowed to react until substantially complete, as indicated by TLC. The titled compound is concentrated under reduced pressure to provide a crude material which is used without further purification.

The titled compound may also be prepared by adding trifluoroacetic acid to a cold (0° C.) solution of the titled compound of Example 1 in methylene chloride. The resulting reaction mixture is reacted for approximately 0–40 minutes at 0° C. and then at room temperature until substantially complete, as indicated by TLC. The desired titled compound is isolated using standard techniques and then further purified, if necessary, using flash. chromatography.

EXAMPLE 3

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(ethanoyl)amino-8-benzyloxy]octyl decahydroisoquinoline-3'-carboxamide The titled compound is prepared by adding acetic anhydride to a solution of the titled compound of Example 2, followed by the addition of of pyridine. When the reaction is substantially complete, as indicated by TLC, the reaction mixture is washed with a cold (0° C.) solution of 10N hydrochloric acid. The desired titled compound may then be isolated from the organic layer and, if necessary, further purified using flash chromatography.

The titled compound may also be prepared by adding acetyl chloride to a solution containing the titled compound of Example 2 and triethylamine in methylene chloride, under nitrogen. When the reaction is substantially complete, as indicated by TLC, the reaction mixture is poured into a cold (0° C.) solution of 1N hydrochloric acid. The desired titled compound may then be isolated from the organic layer and, if necessary, further purified using flash chromatography.

EXAMPLE 4

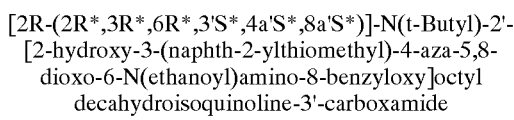

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-carboxy]heptyl decahydroisoquinoline-3'-carboxamide The titled compound is prepared by combining the titled compound of Example 3 with ammonium formate in methanol and in the presence of 5% palladium-on-carbon catalyst. When the reaction is substantially complete, as indicated by TLC, the reaction mixture is filtered and the desired titled compound is isolated from the filtrate and further purified, if necessary, using column chromatography.

EXAMPLE 5

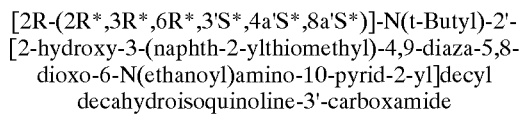

[2R-(2R*,3R*,6R*,3'S*,4a'S*,8a'S*)]-N(t-Butyl)-2'-[2-hydroxy-3-(naphth-2-ylthiomethyl)-4,9-diaza-5,8-dioxo-6-N(ethanoyl)amino-10-pyrid-2-yl]decyl decahydroisoquinoline-3'-carboxamide The titled compound is prepared by adding DCC to a cold (0° C.) solution containing the titled compound of Example 4, 2-(aminomethyl)pyridine and HOBT.H₂O in tetrahydrofuran and dimethylformamide. After slowly warming the resulting reaction mixture to room temperature and then allowing it to react for 1–24 hours, the reaction mixture is diluted with a 15% isopropanol in chloroform solution. The desired titled compound is isolated from the organic layer and further purified, if necessary, using flash chromatography.

EXAMPLE 6

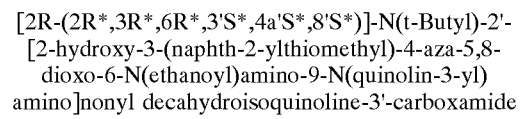

[2R-(2R*,3R*,6R*,3'S*,4a'S*,8'S*)]-N(t-Butyl)-2'-[2-hydroxy-3-(naphth-2-ylthiomethyl)-4-aza-5,8-dioxo-6-N(ethanoyl)amino-9-N(quinolin-3-yl)amino]nonyl decahydroisoquinoline-3'-carboxamide The titled compound is prepared substantially in accordance with the procedure detailed in Example 5 using the titled compound of Example 4, 3-amino-quinoline, HOBT.H₂O and DCC.

EXAMPLE 7

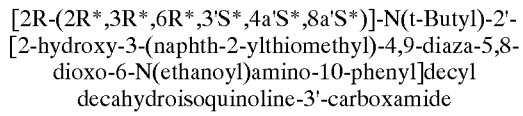

[2R-(2R*,3R*,6R*,3'S*,4a'S*,8a'S*)]-N(t-Butyl)-2'-[2-hydroxy-3-(naphth-2-ylthiomethyl)-4,9-diaza-5,8-dioxo-6-N(ethanoyl)amino-10-phenyl]decyl decahydroisoquinoline-3'-carboxamide The titled compound is prepared substantially in accordance with the procedure detailed in Example 5 using the titled compound of Example 4, benzylamine, HOBT.H₂O and DCC.

EXAMPLE 8

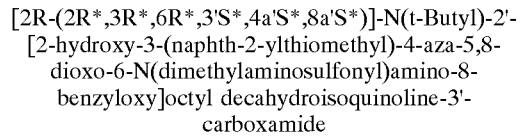

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(dimethylaminosulfonyl)amino-8-benzyloxy]octyl decahydroisoquinoline-3'-carboxamide The titled compound is prepared by adding dimethylsulfamoyl chloride to a solution of the titled compound of Example 2 and triethylamine in methylene chloride, under nitrogen. When the reaction is substantially complete, as indicated by TLC, the reaction mixture is reduced to dryness under reduced pressure to provide a residue. The residue is further purified, if necessary, using column chromatography.

EXAMPLE 9

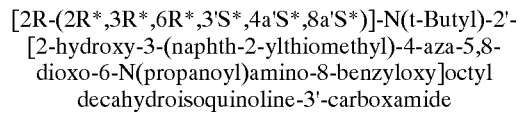

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(propanoyl)amino-8-benzyloxy]octyl decahydroisoquinoline-3'-carboxamide The titled compound is prepared substantially in accordance with the procedure detailed in Example 3, using the

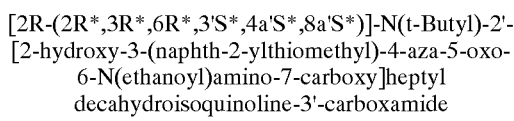

titled compound of Example 2, propionyl chloride and triethylamine in methylene chloride.

EXAMPLE 10

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(butanoyl)amino-8-benzyloxy]octyl decahydroisoquinoline-3'-carboxamide The titled compound is prepared substantially in accordance with the procedure detailed in Example 3, using the titled compound of Example 2, butyryl chloride and triethylamine in methylene chloride.

EXAMPLE 11

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(methylsulfonyl)amino-8-benzyloxy]octyl decahydroisoquinoline-3'-carboxamide The titled compound is prepared substantially in accordance with the procedure detailed in Example 3, using the titled compound of Example 2, methanesulfonylchloride and triethylamine in methylene chloride.

EXAMPLE 12

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(methylsulfonyl)amino-7-carboxy]heptyl decahydroisoquinoline-3'-carboxamide The titled compound is prepared substantially in accordance with the procedure detailed in Example 4, using the titled compound of Example 11, ammonium formate and palladium-on-carbon catalyst in methanol.

EXAMPLE 13

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(methylsulfonyl)amino-8-N(quinolin-2-yl)amino]octyl decahydroisoquinoline-3'-carboxamide The titled compound is prepared substantially in accordance with the procedure detailed in Example 5, using the titled compound of Example 12, 2-aminoquinoline, HOBT.H$_2$O and DCC.

EXAMPLE 14

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(methylsulfonyl)amino-10-benzyl]decyl decahydroisoquinoline-3'-carboxamide The titled compound is prepared substantially in accordance with the procedure detailed in Example 5, using the titled compound of Example 12, benzylamine, HOBT.H$_2$O and DCC.

EXAMPLE 15

[2R-(2R*,3R*,6R*,3'S*,4a'S*,8a'S*)]-N(t-Butyl)-2'-[2-hydroxy-3-(naphth-2-ylthiomethyl)-4,9-diaza-5,8-dioxo-6-N(methylsulfonyl)amino-10-quinolin-2-yl]decyl decahydroisoquinoline-3'-carboxamide The titled compound is prepared substantially in accordance with the procedure detailed in Example 5, using the titled compound of Example 12, 2-aminomethylquinoline, HOBT.H$_2$O and DCC.

EXAMPLE 16

[2R-(2R*,3R*,6R*,3'S*,4a'S*,8a'S*)]-N(t-Butyl)-2'-[2-hydroxy-3-(naphth-2-ylthiomethyl)-4-aza-5,8-dioxo-6-N(methylsulfonyl)amino-8-benzyloxy]octyl decahydroisoquinoline-3'-carboxamide The titled compound is prepared by adding trimethylsilylisocyanate to a solution of the titled compound of Example 2 in tetrahydrofuran. When the reaction is substantially complete, as indicated by TLC, the desired titled compound is isolated using standard techniques and then further purified, if necessary, using flash chromatography.

EXAMPLE 17

[2R-(2R*,3R*,6R*,3'S*,4a'S*,8a'S*)]-N(t-Butyl)-2'-[2-hydroxy-3-(naphth-2-ylthiomethyl)-4-aza-5,8-oxo-6-N(t-butoxycarbonyl)amino-7-benzyloxy]heptyl decahydroisoquinoline-3'-carboxamide The titled compound is prepared substantially in accordance with the procedure detailed in Example 1, using the subtitled compound of Preparation 1G, (R)-2-N(t-butoxycarbonyl)- 3-benzyloxypropanoic acid, HOBT.H$_2$O and DCC.

EXAMPLE 18

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-amino-7-benzyloxy]heptyl decahydroisoquinoline-3'-carboxamide The titled compound is prepared substantially in accordance with Example 2, using the titled compound of Example 17 and trifluoroacetic acid in methylene chloride.

EXAMPLE 19

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-benzyloxy]heptyl decahydroisoquinoline-3'-carboxamide The titled compound is prepared substantially in accordance with Example 3, using the titled compound of Example 18 and acetyl chloride.

EXAMPLE 20

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(methylsulfonyl)amino-7-benzyloxy]heptyl decahydroisoquinoline-3'-carboxamide The titled compound is prepared substantially in accordance with Example 3, using the titled compound of Example 18, methanesulfonylchloride and triethylamine.

EXAMPLE 21

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(t-butoxycarbonyl)amino-7-naphth-2-ylthio]heptyl decahydroisoquinoline-3'-carboxamide The titled compound is prepared substantially in accordance with the procedure detailed in Example 1, using the subtitled compound of Preparation 1G, (S)-2-N(t-butoxycarbonyl)amino-3-naphth-2-ylthiopropanoic acid, HOBT.H₂O and DCC.

EXAMPLE 22

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-amino-7-naphth-2-ylthio]heptyl decahydroisoquinoline-3'-carboxamide The titled compound is prepared substantially in accordance with the procedure detailed in Example 2, using the titled compound of Example 21 and trifluoroacetic acid.

EXAMPLE 23

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-naphth-2-ylthio]heptyl decahydroisoquinoline-3'-carboxamide The titled compound is prepared substantially in accordance with the procedure detailed in Example 3, using the titled compound of Example 22 and acetyl chloride.

EXAMPLE 24

A. (S)-2-N(ethanoyl)amino-3-naphth-2-ylthio propanoic acid

To a solution of (S)-2-N(t-butoxycarbonyl)amino-3-naphth-2-ylthio propanoic acid in 4 mL of methylene chloride, was added 4 mL of trifluoroacetic acid. The resultant reaction mixture was allowed to react at room temperature for approximately 2 hours. When the reaction was substantially complete, as indicated by TLC, the reaction mixture was concentrated under reduced pressure to provide 1.13 g of a solid. This solid was then redissolved in 10 mL of water to provide a solution which was basified to about pH 10 using a 1N sodium hydroxide solution and then cooled to 0° C. To the resultant solution was then slowly added 0.6 mL of acetic anhydride, while maintaining the solution at pH 8–9 by the addition of a 1N sodium hydroxide solution. The resultant reaction mixture was warmed to room temperature and allowed to react for approximately twenty minutes and then cooled to 0° C. and acidified to pH 3 using a 1N hydrochloric acid solution. The desired subtitled compound was then extracted into ethyl acetate, dried over sodium sulfate and then concentrated under reduced pressure to provide an oil. This oil was recrystallized from a deuterated chloroform/methylene chloride solution to provide a solid. This solid was triturated with hexanes and then reduced to dryness under reduced pressure to provide 0.71 g of an off-white solid.

Analysis for $C_{15}H_{15}NO_3S$: Calcd: C, 62.27; H, 5.23; N, 4.84; Found: C, 61.99; H, 5.31; N, 4.90.

B. (S)-2-N(ethanoyl)amino-3-naphth-2-ylsulfonyl propanoic acid

To a cold (0° C.) solution of 0.23 g (0.795 mmol) of the subtitled compound of Example 24A in 2 mL of methanol, was added a solution of 0.58 g (2.78 mmol) of oxone® in 2 mL of water. The resultant reaction mixture was allowed to react for approximately fifteen minutes, warmed to room temperature and then reacted for an additional two hours. The reaction mixture was then sonicated for fifteen minutes and concentrated under reduced pressure. The desired subtitled compound was then extracted into methylene chloride, dried over sodium sulfate, filtered and then concentrated under reduced pressure to provide 130 mg of an off-white solid.

Analysis for $C_{15}H_{15}NO_5S$: Calcd: C, 56.07; H, 4.71; N, 4.36; Found: C, 56.26; H, 4.66; N, 4.15.

C. [2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-naphth-2-ylsulfonyl]heptyl decahydroisoquinoline-3'-carboxamide The subtitled compound is prepared substantially in accordance with the procedure detailed in Example 1, using subtitled intermediate of Preparation 1G, the subtitled compound of Example 24B, HOBT.H₂O and of DCC to provide crude material. This material is purified using flash chromatography the desired subtitled compound.

EXAMPLE 25

A. (S)-2-N(ethanoyl)amino-3-naphth-2-ylsulfonyl propanoic acid

The subtitled compound is prepared substantially in accordance with the procedure detailed in Example 24B, using the subtitled compound of Example 24A and 1 equivalent of oxone®.

B. [2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-naphth-2-ylsulfonyl]heptyl decahydroisoquinoline-3'-carboxamide The subtitled compound is prepared substantially in accordance with the procedure detailed in Example 1, using the subtitled intermediate of Preparation 1G, the subtitled compound of Example 25A, HOBT.H₂O and DCC.

EXAMPLE 26

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(methylsulfonyl)amino-7-naphth-2-ylthio]heptyl decahydroisoquinoline-3'-carboxamide The titled compound is prepared substantially in accordance with the procedure detailed in Example 3, using the titled compound of Example 22 and methanesulfonylchloride.

EXAMPLE 27

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-indol-3-yl]heptyl decahydroisoquinoline-3'-carboxamide The titled compound is prepared substantially in accordance with the procedure detailed in Example 1, using the subtitled compound of Preparation 1G, (R)-2-N(ethanoyl)amino-3-indol-3-ylpropanoic acid, HOBT.H₂O and DCC.

EXAMPLE 28

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-phenyl]heptyl decahydroisoquinoline-3'-carboxamide The titled compound is prepared substantially in accordance with the procedure detailed in Example 1, using the subtitled compound of Preparation 1G, (R)-2-N(ethanoyl)-amino-3-phenylpropanoic acid, HOBT.H₂O and DCC.

EXAMPLE 29

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-naphth-2-ylcarbonyloxy]heptyl decahydroisoquinoline-3'-carboxamide The titled compound is prepared substantially in accordance with the procedure detailed in Example 1, using the subtitled compound of Preparation 1G, (2R)-2-N(t-butoxycarbonyl)amino-3-naphth-2-ylcarbonyloxy-propanoic acid, HOBT.H₂O and DCC.

EXAMPLE 30

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-amino-7-naphth-2-ylcarbonyloxy]heptyl decahydroisoquinoline-3'-carboxamide The titled compound is prepared substantially in accordance with the procedure detailed in Example 2, using the titled compound of Example 29 and trifluoroacetic acid.

EXAMPLE 31

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-naphth-2-ylcarbonyloxy]heptyl decahydroisoquinoline-3'-carboxamide The titled compound is prepared substantially in accordance with the procedure detailed in Example 3, using the titled compound of Example 30, acetyl chloride and triethylamine.

EXAMPLE 32

[2R-(2R*,3R*,6R*,3'S*,4a'S*,8a'S*)]-N(t-Butyl)-2'-[2-hydroxy-3-(naphth-2-ylthiomethyl)-4-aza-5-oxo-6-N(ethanoyl)amino-7-phenylmethylthio]heptyl decahydroisoquinoline-3'-carboxamide The titled compound is prepared substantially in accordance with the procedure detailed in Example 1, using the subtitled compound of Preparation 1G, (2R)-2-N(ethanoyl) amino-3-phenylmethylthio propanoic acid, HOBT.H₂O and DCC.

The reactions described above in Examples 1–33 is carried out using the subtitled intermediate from Preparation 2G or the subtitled intermediate from Preparation 3B as starting material (reactant IA in Reaction I). For example, the subtitled intermediate of Preparation 2G is reacted with (2R)-2-N(t-butoxycarbonyl)amino-4-oxo-4-benzyloxybucanoic acid to provide [2R-(2R*,3R*,6R*,3'S*,4a'S*,8a'S*)]-N(t-butyl)-2'-[2-hydroxy-3-phenylthiomethyl-4-aza-5,8-dioxo-6-N(t-butoxycarbonyl)-amino-8-benzyloxy]octyl decahydroisoquinoline-3'-carboxamide.

EXAMPLE 33

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-phenylmethylthio]heptyl decahydroisoquinoline-3'-carboxamide To a solution containing 63 mg (0.249 mmol) of (R)-2-N(ethanoyl)amino-3-phenylmethylthio propanoic acid, 0.10 mg (0.249 mmol) of the subtitled intermediate of Preparation 3B and 34 mg (0.249 mmol) of HOBT.H₂O, was added 51 mg (0.249 mmol) of DCC. The resulting reaction mixture was allowed to react overnight at room temperature, resulting in the formation of a precipitate. This precipitate was removed by filtration. The precipitate was rinsed with ethyl acetate and the filtrate was then reduced to dryness under reduced pressure to provide 0.17 g of a white solid. This solid was purified using flash chromatography (gradient eluent of 4–10% methanol in methylene chloride), followed by preparatory HPLC (gradient eluent of 70–80% methanol in water containing 0.5% ammonium acetate) to provide 70 mg of an off-white solid.

¹H NMR (CDCl₃): δ1.30 (s, 9H), 1.2–2.0 (m, 15H), 1.92 (s, 3H), 2.21 (m, 1H), 2.38 (m, 1H), 2.60 (m, 2H), 2.85–3.05 (m, 3H), 3.58 (q, J=8 Hz, 2H), 3.90 (m, 1H), 4.35 (m, 1H), 4.51 (m, 1H), 5.90 (br.s, 1H), 6.42 (d, J=8 Hz, 1H), 7.10–7.32 (m, 10H).

MS (FD): 638 (M⁺¹).

Analysis for C₃₆H₅₂N₄O₄S: Calcd: C, 67.89; H, 8.23; N, 8.80; Found: C, 67.60; H, 8.22; N, 8.70.

EXAMPLE 34

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-phenylmethylsulfinyl]heptyl decahydroisoquinoline-3'-carboxamide The titled compound is prepared by slowly adding one equivalent of oxone® in water to a cold (0° C.) solution containing one equivalent of the titled compound of Example 33 in methanol. The desired titled compound is isolated using standard techniques and then further purified, if necessary, using flash chromatography.

The titled compound may also be prepared by adding one equivalent of m-chloroperoxybenzoic acid (MCPBA) to a cold (0° C.) solution containing one equivalent of the titled compound of Example 33 in methylene chloride. The desired titled compound is isolated using standard techniques and then further purified, if necessary, using flash chromatography.

EXAMPLE 35

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-phenylmethylsulfinyl]heptyl decahydroisoquinoline-3'-carboxamide The titled compound may also be prepared by slowly adding two equivalents of oxone® in water to a cold (0° C.) solution containing one equivalent of the titled compound of Example 33 in methanol. The desired titled compound is isolated using standard techniques and then further purified, if necessary, using flash chromatography.

The titled compound may also be prepared by adding two equivalents of m-chloroperoxybenzoic acid (MCPBA) to a cold (0° C.) solution containing one equivalent of the titled compound of Example 33 in methylene chloride. The desired titled compound is isolated using standard techniques and then further purified, if necessary, using flash chromatography.

EXAMPLE 36

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-naphth-2ylsulfonyl]heptyl decahydroisoquinoline-3'-carboxamide The titled compound was prepared substantially in accordance with the procedure detailed in Example 1, using 88 mg (0.219 mmol) of the subtitled intermediate of Preparation 3B, 70 mg (0.219 mmol) of the subtitled compound of Example 24B, 30 mg (0.219 mmol) of HOBT.H$_2$O and 45 mg (0.219 mmol) of DCC to provide 130 mg of crude material. This material was purified using flash chromatography (gradient eluent of 4–10% methanol in methylene chloride) to provide 30 mg of a white solid.

Yield: 20%.

MS (FD): 705 (M$^+$).

EXAMPLE 37

A. [2R-(2R*,3R*,6R*,3'S*,4a'S*,8a'S*)]-N(t-Butyl)-2'-[2-hydroxy-3-phenylmethyl-4-aza-5-oxo-6-N(t-butoxycarbonyl)amino-7-p-fluoro-phenylthio] heptyl decahydroisoquinoline-3'-carboxamide The subtitled compound was prepared substantially in accordance with the procedure detailed in Example 33, using 0.17 g (0.55 mmol) of S-2-N(t-butoxycarbonyl)amino-3-p-fluoro-phenylthio propanoic acid, 0.22 g (0.55 mmol) of the subtitled intermediate of Preparation 3B and 0.07 g (0.55 mmol) of HOBT.H$_2$O, and 0.11 g (0.55 mmol) of DCC in 4 mL of tetrahydrofuran and 0.5 mL of dimethylformamide to provide 0.39 g of a white solid.

Yield: 100%.

MS (FD): m/e 699 (M$^+$).

B. [2R-(2R*,3R*,6R*,3'S*,4a'S*,8a'S*)]-N(t-Butyl)-2'-[2-hydroxy-3-phenylmethyl-4-aza-5-oxo-6-N(t-butoxycarbonyl)amino-7-p-fluoro-phenylthio]heptyl decahydroisoquinoline-3'-carboxamide To a solution of 0.38 g (0.54 mmol) of the subtitled compound of Example 37A in 3 mL of methylene chloride, was added 3 mL of trifluoroacetic acid. The resultant reaction mixture was reacted for approximately one hour at room temperature and then was concentrated under reduced pressure to provide a residue. This residue was redissolved in ethyl acetate, and washed sequentially with ammonium hydroxide, water, and brine, dried over sodium sulfate, filtered and then concentrated under reduced pressure to provide 0.30 g of an off-white solid. This solid was purified using flash chromatography (eluent of 8% methanol in methylene chloride) to provide 0.20 g of a white solid.

Yield: 61%.

MS (FD): m/e 599 (M$^+$).

C. [2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylthio]heptyl decahydroisoquinoline-3'-carboxamide To a solution of 1.05 g (0.175 mmol) of the subtitled compound of Example 37B, and 0.49 mL (3.5 mmol) of triethylamine in 5 mL of methylene chloride, was added 16 mL (2.10 mmol) of mechanesulfamoyl chloride, under nitrogen. When the reaction is substantially complete, as indicated by TLC, the reaction mixture was concentrated under reduced pressure and then redissolved in ethyl acetate and washed sequentially with sodium bicarbonate, and brine, dried over sodium sulfate, filtered and concentrated under reduced pressure to provide 1.2 g of a white solid. This solid was purified using flash chromatography (eluent of 3.5% methanol in methylene chloride) to provide 0.70 g of a white solid.

Yield: 58%.

Analysis for C$_{34}$H$_{49}$FN$_4$O$_5$S$_2$H$_2$O: Calcd: C, 58.76; H, 7.40; N, 8.06; Found: C, 59.15; H, 7.18; N, 8.01.

EXAMPLE 38

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylsulfinyl] heptyl decahydroisoquinoline-3'-carboxamide To a cold (0° C.) solution of 0.10 g (0.15 mmol) of the subtitled compound of Example 37C in 3 mL of methanol, was added a solution of 71 mg (0.34 mmol) of oxone® in 2 mL of water. When the reaction was substantially complete, as indicated by TLC, the reaction mixture was diluted with a methylene chloride/water mixture. The resulting layers were separated and the organic layer was washed with brine, dried over sodium sulfate, filtered and then concentrated under reduced pressure to provide 100 mg of a white solid. This solid was purified using flash chromatography (silica; eluent of 10% methanol in methylene chloride) to provide 50 mg of the desired titled compound.

Yield: 50%.

$^1$H NMR (CDCl$_3$): 1.30 (s, 9H), 1.1–2.4 (m, 17H), 2.60 (m, 4H), 2.80 (dd, J=8 Hz, 1H), 2.98 (s, 3H), 3.80 (m, 1H), 4.30 (m, 1H), 4.48 (m, 1H), 5.75 (d, J=8 Hz, 1H), 6.18 (br.s, 1H), 6.81 (m, 3H), 7.00 (d, J=8 Hz, 2H), 7.37 (t, J=8 Hz, 2H), 7.60 (m, 2H), 8.10 (d, J=8 Hz, 1H).

EXAMPLE 39

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylsulfonyl] heptyl decahydroisoquinoline-3'-carboxamide The titled compound was prepared substantially in accordance with the procedure detailed in Example 38, using 0.80 g (1.13 mmol) of the subtitled compound of Example 37C in 5 mL of methanol, and 1.13 g (5.42 mmol) of oxone® in 5 mL of water to provide a crude material. This material was purified using reverse phase HPLC (eluent of 35% methanol/35% acetonitrile/30% water/0.5% ammonium acetate) to provide 0.84 g of a white solid.

Yield: 56%.

$^1$H NMR (CDCl$_3$): δ1.30 (s, 9H), 1.1–2.0 (m, 14H), 2.30 (m, 2H), 2.62 (m, 2H), 2.88 (s, 3H), 2.8–3.1 (m, 4H), 3.18 (m, 1H), 3.96 (m, 1H), 4.35 (m, 1H), 4.55 (m, 1H), 6.19 (br.s, 1H), 7.00 (r, J=8 Hz, 1H), 7.12 (m, 4H), 7.23 (t, J=8 Hz, 2H), 7.49 (d, J=9 Hz, 1H), 7.94 (m, 2H).

EXAMPLE 40

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylsulfonyl] heptyl decahydroisoquinoline-3'-carboxamide A solution of 40 μL of methanesulfonic acid in 100 mL of methylene chloride was slowly added to a solution of 437 mg (0.616 mmol) of the titled compound of Example 39 in 5 mL of methylene chloride. The resultant reaction mixture was reduced to dryness under reduced pressure to provide 487 mg of the desired titled compound.

MS (FD): m/e 710 (M$^+$).

Analysis for C$_{35}$H$_{53}$FN$_4$O$_{10}$S$_3$: Calcd: C, 52.22; H, 6.64; N, 6.96; Found: C, 51.96; H, 6.39; N, 6.79.

EXAMPLE 41

A. [2R-(2R*,3S,6S*,3'S*,4a'S*,8a'S*)]-N(t-Butyl)-2'-[2-hydroxy-3-phenylmethyl-4-aza-5-oxo-6-N(t-butoxycarbonyl)amino-7-naphth-2-ylthio]heptyl decahydroisoquinoline-3'-carboxamide The subtitled compound was prepared substantially in accordance with the procedure detailed in Example 33, using 0.41 g (0.12 mmol) of S-2-N(t-butoxycarbonyl) amino- 3-naphth-2-ylthio propanoic acid, 0.47 g (0.12 mmol) of the subtitled intermediate of Preparation 3B and 0.16 g (0.12 mmol) of HOBT.H$_2$O, and 0.24 g (0.12 mmol) of DCC in 8 mL of tetrahydrofuran and 0.5 mL of dimethylformamide to provide 0.86 g of crude material. This material was purified using flash chromatography (eluent of 10% methanol in methylene chloride) followed by flash chromatography (eluent of 3.5% methanol in methylene chloride) to provide 0.45 g of a white solid.

Yield: 52%.

MS (FD): m/e 731 (M$^+$).

Analysis for C$_{42}$H$_{58}$N$_4$O$_5$S: Calcd: C, 69.01; H, 8.00; N, 7.66; Found: C, 68.80; H, 8.03; N, 7.93.

B. [2R-(2R*,3R*,6R*,3'S*,4a'S*,8a'S*)]-N(t-Butyl)-2'-[2-hydroxy-3-phenylmethyl-4-aza-5-oxo-6-amino-7-naphth-2-ylthio]heptyl decahydroisoquinoline-3'-carboxamide The subtitled compound was prepared substantially in accordance with the procedure detailed in Example 37B, using 0.45 g (0.62 mmol) of the subtitled compound of Example 41A, and 4 mL of trifluoroacetic acid in 4 mL of methylene chloride to provide 0.39 g of the desired subtitled compound.

Yield: 100%.

MS (FD): m/e 631 (M$^+$).

C. [2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylthio]heptyl decahydroisoquinoline-3'-carboxamide The desired subtitled compound was prepared substantially in accordance with the procedure detailed in Example 37C, using 0.39 g (0.62 mmol) of the subtitled compound of Example 41B, 172 μL (0.124 mmol) of triethylamine and 68 μL (0.87 mmol) of methanesulfonyl chloride to provide 0.43 g of crude material. This material was purified using flash chromatography (gradient eluent of 3.5–4% methanol in methylene chloride) to provide 0.19 g of a white solid.

Yield: 43%.

MS (FD): 709.

Analysis for C$_{38}$H$_{52}$N$_4$O$_5$S$_2$: Calcd: C, 64.38; H, 7.39; N, 7.90; Found: C, 64.54; H, 7.50; N, 7.72.

EXAMPLE 42

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylsulfinyl]heptyl decahydroisoquinoline-3'-carboxamide The desired subtitled compound was prepared substantially in accordance with the procedure detailed in Example 38, using 0.15 g (0.21 mmol) of the subtitled compound of Example 41C, and 102 mg (0.486 mmol) of oxone® to provide 0.14 g of the desired compound.

Yield: 93%.

MS (FD): m/e 725 (M$^+$).

EXAMPLE 43

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylsulfinyl]heptyl decahydroisoquinoline-3'-carboxamide The desired subtitled compound was prepared substantially in accordance with the procedure detailed in Example 40, using 66 mg (0.091 mmol) of the subtitled compound of Example 42C, and 6 μL of methanesulfonic acid in 3 mL of methylene chloride to provide 75 mg of a white solid.

Yield: 100%.

Analysis for C$_{38}$H$_{52}$N$_4$O$_5$S$_2$: Calcd: C, 54.13; H. 6.70; M, 6.38; Found: C, 54.19; H, 6.61; N, 6.43.

EXAMPLE 44

[2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylsulfonyl]heptyl decahydroisoquinoline-3'-carboxamide The titled compound was prepared substantially in accordance with the procedure detailed in Example 33, using 89 mg (0.25 mmol) of S-2-N(methylsulfonyl)amino-3-naphth-2-ylsulfonyl propanoic acid, 100 mg (0.25 mmol) of the subtitled intermediate of Preparation 3B and 34 mg (0.25 mmol) of HOBT.H$_2$O, and 51 mg (0.25 mmol) of DCC in 6 mL of anhydrous tetrahydrofuran to provide 0.18 g of a white solid. This solid was purified using flash chromatography (eluent of 4% methanol in methylene chloride) to provide 39 mg of an off-white solid.

Yield: 22%.

MS (FD): m/e 741 (M$^+$)

EXAMPLE 45

[2'S-(2'R*,2S*,3R*,6R*)]-1'-[(2-Hydroxy-3-phenylmethyl-4-aza-5-oxo-6-N-(methylsulfonyl)amino-7-p-fluorophenylsulfonyl)heptyl]-4-pyrid-3"-ylmethyl decahydroisoquinoline-3'-carboxamide The titled compound was prepared substantially in accordance with the procedure detailed in Example 33, using 94 mg (0.29 mmol) of S-2-N(methylsulfonyl)amino-3-p-fluorophenylsulfonyl propanoic acid, 127 mg (0.289 mmol) of the subtitled intermediate of Preparation 7E and 39 mg (0.29 mmol) of HOBT.H$_2$O, was added 60 mg (0.29 mmol) of DCC in 4 mL of tetrahydrofuran to provide 0.17 g of crude material. This material was purified using flash chromatography (eluent of 8% methanol in methylene chloride containing 0.2% ammonium hydroxide) to provide 49 mg of the desired titled compound.

Yield: 22%

MS (FD): m/e 748 (M$^+$).

EXAMPLE 46

[2'S-(2'R*,2S*,3R*,6R*)]-1'-[(2-Hydroxy-3-phenylmethyl-4-aza-5-oxo-6-N-(methylsulfonyl)amino-7-p-fluorophenylsulfonyl)heptyl]-4-pyrid-3"-ylmethyl decahydroisoquinoline-3'-carboxamide methanesulfonate The desired subtitled compound was prepared substantially in accordance with the procedure detailed in Example, using 16 μL (0.24 mmol) of methanesulfonic acid, and 60 mg (0.0.080 mmol) of the titled compound of Example 45 in 50 mL of methylene chloride. The resultant reaction mixture was reduced to dryness under reduced pressure to provide 75 mg of a white hygroscopic solid.

MS (FD): m/e 748.

Analysis for C$_{35}$H$_{47}$FN$_6$O$_7$S$_2$.3CH$_3$SO$_3$H: Calcd: C, 44.09; H, 5.74; N, 8.12; Found: C, 44.29; H, 5.58; N, 8.07.

EXAMPLE 47

A. [2R-(2R*,3R*,6R*,3'S*,4a'S*,8a'S*)]-N(t-Butyl)-2'-[2-hydroxy-3-phenylmethyl-4-aza-5-oxo-6-N(t-butoxycarbonyl)amino-7-p-fluoro-phenylsulfonyl]heptyl decahydroisoquinoline-3'-carboxamide The subtitled compound was prepared substantially in accordance with the procedure detailed in Example 33, using 92 mg (0.27 mmol) of S-2-N(t-butoxycarbonyl) amino-3-p-fluoro-phenylsulfonyl propanoic acid, 115 mg (0.27 mmol) of the subtitled intermediate of Preparation 2G and 36 mg (0.27 mmol) of HOBT.H$_2$O, and 55 mg (0.27 mmol) of DCC in 3 mL of tetrahydrofuran to provide 0.20 g of a tan solid. This solid was purified using flash chromatography (eluent of 4% methanol in methylene chloride) to provide 0.16 g of an off-white solid.

Yield: 79%.

MS (FD): m/e 764 (M$^{+1}$).

B. [2R-(2R*,3R*,6R*,3'S*,4a'S*,8a'S*)]-N(t-Butyl)-2'-[2-hydroxy-3-phenylmethyl-4-aza-5-oxo-6-amino-7-p-fluoro-phenylsulfonoyl]heptyl decahydroisoquinoline-3'-carboxamide The subtitled compound was prepared substantially in accordance with the procedure detailed in Example 37B, using 0.16 g (0.21 mmol) of the subtitled compound of Example 47A, and 2 mL of trifluoroacetic acid in 2 mL of methylene chloride to provide 0.13 g of the desired subtitled compound.

Yield: 94%.

C. [2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylsulfonyl] heptyl decahydroisoquinoline-3'-carboxamide The desired subtitled compound was prepared substantially in accordance with the procedure detailed in Example 37C, using 0.13 g (0.20 mmol) of the subtitled compound of Example 47B, and 18.2 μL (0.235 mmol) of methanesulfamoyl chloride, and 47.4 μL (0.431 mmol) of N-methylmorpholine in 3 mL of methylene chloride, to provide 0.16 g of crude material. This material was purified using flash chromatography (eluent of 3.5% methanol in methylene chloride) to provide 30 mg of the subtitled compound.

Yield: 21%.

$^1$H NMR (CDCl$_3$): δ1.38 (s, 9H), 1.1–2.3 (m, 14H), 2.50 (d, J=8 Hz, 1H), 2.62 (t, J=6 Hz, 1H), 2.92 (d, J=8 Hz, 1H), 3.10 (s, 3H), 3.25 (dd, J=4,8 Hz, 1H), 3.43 (m, 1H), 3.62 (m, 2H), 4.11 (m, 1H), 4.30 (m, 1H), 4.70 (m, 1H), 5.65 (br.s, 1H), 7.10–7.30 (m, 5H), 7.40 (d, J=8 Hz, 2H), 7.98 (m, 1H), 8.08 (d, J=8 Hz, 1H).

EXAMPLE 48

A. [2R-(2R*,3R*,6R*,3'S*,4a'S*,8a'S*)]-N(t-Butyl)-2'-[2-hydroxy-3-phenylmethyl-4-aza-5-oxo-6-N(t-butoxycarbonyl)amino-7-naphth-2-ylsulfonyl] heptyl decahydroisoquinoline-3'-carboxamide The subtitled compound was prepared substantially in accordance with the procedure detailed in Example 33, using 118 mg (0.311 mmol) of S-2-N(t-butoxycarbonyl) amino-3-naphth-2-ylsulfonyl propanoic acid, 135 mg (0.311 mmol) of the subtitled intermediate of Preparation 2G and 42 mg (0.31 mmol) of HOBT.H$_2$O, and 64 mg (0.31 mmol) of DCC in 3 mL of tetrahydrofuran to provide 0.23 g of crude material. This material was purified using flash chromatography (eluent of 2.5% methanol in-methylene chloride) to provide 0.18 g of a white solid.

Yield: 73%.

B. [2R-(2R*,3R*,6R*,3'S*,4a'S*,8a'S*)]-N(t-Butyl)-2'-[2-hydroxy-3-phenylmethyl-4-aza-5-oxo-6-N(t-butoxycarbonyl)amino-7-naphth-2-ylsulfonyl]heptyl decahydroisoquinoline-3'-carboxamide The subtitled compound was prepared substantially in accordance with the procedure detailed in Example 37B, using 0.18 g (0.23 mmol) of the subtitled compound of Example 48A, and 2 mL of trifluoroacetic acid in 2 mL of methylene chloride to provide 0.15 g of a tan solid. This solid was used with further purification.

Yield: 94%.

C. [2R-(2R*,3R*,6R*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylsulfonyl]heptyl decahydroisoquinoline-3'-carboxamide The subtitled compound was prepared substantially in accordance with the procedure detailed in Example 37C, using 0.15 g (0.22 mmol) of the subtitled compound of Example 48B, and 28 μL (0.367 mmol) of methanesulfamoyl chloride, and 55 μL (0.50 mmol) of N-methylmorpholine in 2 mL of methylene chloride, to provide 0.18 g of crude material. This material was purified using flash chromatography (gradient eluent of 1.5–5% methanol in methylene chloride) to provide 30 mg of the desired subtitled compound.

Yield: 18%.

MS (FD): m/e 774 (M$^{+1}$).

$^1$H NMR (CDCl$_3$): δ1.38 (s, 9H), 1.1–1.8 (m, 11H), 2.00 (m, 1H), 2.20 (m, 2H), 2.50 (d, J=8 Hz, 1H), 2.65 (m, 1H), 2.92 (d, J=8 Hz, 1H), 3.12 (m, 3H), 3.25 (dd, J=4,8 Hz, 1H), 3.40 (m, 1H), 3.65 (dd, J=4,8 Hz, 1H), 3.75 (m, 1H), 4.08 (m, 1H), 4.28 (m, 1H), 4.75 (m, 1H), 5.75 (br.s, 1H), 6.32 (br.s, 1H), 7.10 (t, J=6 Hz, 1H), 7.20 (d, J=6 Hz, 2H), 7.35 (d, J=6 Hz, 2H), 7.65 (m, 2H), 7.88–8.02 (m, 5H), 8.55 (br.s, 1H).

EXAMPLE 49

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-phenylmethylthio]heptyl decahydroisoquinoline-3'-carboxamide To a solution containing 63 mg (0.249 mmol) of (S)-2-N(ethanoyl)amino-3-phenylmethylthio propanoic acid, 0.10 mg (0.249 mmol) of the subtitled intermediate of Preparation 3B and 34 mg (0.249 mmol) of HOBT.H$_2$O, was added 51 mg (0.249 mmol) of DCC. The resulting reaction mixture was allowed to react overnight at room temperature, resulting in the formation of a precipitate. This precipitate was removed by filtration. The precipitate was rinsed with ethyl acetate and the filtrate was then reduced to dryness under reduced pressure to provide 0.17 g of a white solid. This solid was purified using flash chromatography (gradient eluent of 4–10% methanol in methylene chloride), followed by preparatory HPLC (gradient eluent of 70–80% methanol in water containing 0.5% ammonium acetate) to provide 70 mg of an off-white solid.

$^1$H NMR (CDCl$_3$): δ1.30 (S, 9H), 1.2–2.0 (m, 15H), 1.92 (s,3H), 2.21 (m, 1H), 2.38 (m, 1H), 2.60 (m, 2H), 2.85–3.05 (m, 3H), 3.58 (q, J=8 Hz, 2H), 3.90 (m, 1H), 4.35 (m, 1H), 4.51 (m, 1H), 5.90 (br. s, 1H), 6.42 (d, J=8 Hz, 1H), 7.10–7.32 (m, 10H).

MS (FD): 638 (M$^{+1}$).

Analysis for C$_{36}$H$_{52}$N$_4$O$_4$S: Calcd: C, 67.89; H, 8.23; N, 8.80; Found: C, 67.60; H, 8.22; N, 8.70.

EXAMPLE 50

[2R-(2R*,3R*,6R*,3'S*,4a'S*,8a'S*)]-N(t-Butyl)-2'-[2-hydroxy-3-phenylmethyl-4-aza-5-oxo-6-N(ethanoyl)amino-7-phenylmethylsulfinyl]heptyl decahydroisoquinoline-3'-carboxamide The titled compound is prepared by slowly adding one equivalent of oxone® in water to a cold (0° C.) solution containing one equivalent of the titled compound of Example 49 in methanol. The desired titled compound is isolated using standard techniques and then further purified, if necessary, using flash chromatography.

EXAMPLE 51

[2R-(2R*,3R*,6R*,3'S*,4a'S*,8a'S*)]-N(t-Butyl)-2'-[2-hydroxy-3-phenylmethyl-4-aza-5-oxo-6-N (ethanoyl)amino-7-phenylmethylsulfonyl]heptyl decahydroisoquinoline-3'-carboxamide The titled compound is prepared by slowly adding two equivalents of oxone® in water to a cold (0° C.) solution containing one equivalent of the titled compound of Example 49 in methanol. The desired titled compound is isolated using standard techniques and then further purified, if necessary, using flash chromatography.

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula I or a pharmaceutically acceptable salt thereof.

The term "effective amount" as used herein, means an amount of a compound of the present invention which is capable of inhibiting the HIV protease mediated viral component production and assembly. The HIV protease inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body-weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 | mg |
|---|---|---|
| Sodium carboxymethyl cellulose | 50 | mg |
| Syrup | 1.25 | mL |
| Benzoic acid solution | 0.10 | mL |
| Flavor | q.v. | |
| Color | q.v. | |
| Purified water to total | 5 | mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 | mg |
|---|---|---|
| Isotonic saline | 1,000 | mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:

BSA—bovine serum albumin
BOC—t-butyloxycarbonyl
BrZ—2-bromobenzyloxycarbonyl
2-ClZ—2-chlorobenzyloxycarbonyl
DCC—dicyclohexylcarbodiimide
DIEA—diisopropylethylamine
DTT—dithiothreitol
EDTA—ethylenediaminetetraacetic acid
FITC—fluorescein isothiocarbamyl
HEPES—4-(2-hydroxyethyl)-1-piperazine-ethanesulfonic acid
MES—4 morpholineethanesulfonic acid
PAM—phenylacetimidomethyl
TAPS—3-[tris(hydroxymethyl)methyl]amino-1-sulfonic acid
TRIS—tris(hydroxymethyl)aminomethane
TOS—p-toluenesulfonyl (tosyl)

I. Preparation of Protease and Gag Fractions

A. Culture of *E. coli* K12 L507/pHP10D

Lyophils of *E. coli* K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 mL LB medium (10 g Bactotryptone, 5 g Bacto-yeast extract, and 10 g sodium chloride per liter; the pH was adjusted to 7.5 and incubated at 32° C., overnight).

A small portion of the overnight culture was placed on LB-agar (LB medium with 15 g/L Bacto-agar) plates containing 12.5 μg/mL tetracycline in a manner so as to obtain a single colony isolate of E. coli K12 L507/pHP10D. The single colony obtained was inoculated into 10 mL of LB medium containing 12.5 μg/mL tetracycline and incubated overnight at 32° C. with vigorous shaking. The 10 mL overnight culture was inoculated into LB medium containing 12.5 μg/mL tetracycline and incubated at 32° C. with vigorous shaking until the culture reached mid-log phase.

B. Culture of E. coli K12 L507/pHGAG

Lyophils of E. coli K12 L507/pHGAG were obtained from the NRRL under the accession number NRRL B-18561 (deposited Nov. 14, 1989). A purified colony of E. coli K 12 L507/pHGAG was isolated, and used as an inoculum for a culture which was grown to mid-log phase in substantial accordance with the teaching of Step A, above, for E. Coli K12 L507/pHP10D.

C. Preparation of Protease Fraction

A culture of E. coli K12 L507/pHP10D was grown to mid-log phase at 32° C. in LB media containing 12.5 μg/mL tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M sodium chloride in Buffer A over 120 min. Enzymatic activity was measured by HPLC using the synthetic peptide Ser-Gln-Asn-Tyr-Pro-Ile-Val as described in Margolin et al., *Biochem. Biophys. Res. Commun.*, 167, 554–560 (1990); the production of the p1 peptide (Ser-Gln-Asn-Tyr) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M sodium chloride in Buffer A over 40 min. The column was washed isocratically in Buffer A containing 0.45M sodium chloride for 30 min.

The active fractions were combined and concentrated to 200 μL using an Amicon stirred cell and a YM-10 membrane and then the protease was applied to a Superose 6 size exclusion column equilibrated in Buffer A containing 0.1M sodium chloride. The column was washed isocratically in this buffer at a flow rate of 0.5 mL/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. Preparation of Gag Fraction

In an analogous manner, a culture of E. coli K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis-buffer was comprised of 50 mM Tris-HCl (pH 7.8), 5 mM EDTA, 1 mM DTT, 100 mM NaCl, 1 μg/mL E64 and 2 μg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

II. Preparation of Substrate: $N^\alpha$-Biotin-Gly-Ser-Gln-Asn-Tyr-Pro-Ile-Val-Gly-Lys($N^\epsilon$-FITC)—OH A. Preparation of the Amino-Terminal Biotinylated Peptide The protected peptide-resin, $N^\alpha$-Boc-Gly-Ser-Gln-Asn-Tyr(BrZ)-Pro-Ile-Val-Gly-Lys(2-ClZ)-OCH$_2$-PAM-resin, was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% di(isopropyl) ethylamine (DIEA) in methylene chloride Then, 1.1 g (4.5 mmol) of biotin in 20 mL of dimethylsulfoxide was added to the peptide resin, followed by 4.5 mmol of dicyclohexyl-carbodiimide (DCC) in 9 mL of methylene chloride. The resulting reaction mixture was diluted to 40 mL total volume using 11 mL methylene chloride, and then allowed to react for approximately 5 hours. The reaction solution was concentrated, the resin washed sequentially with dimethyl-sulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL of diethylether. The peptide was then solubilized in 50% aqueous acetic acid, frozen and lyophilized to provide 2.14 g.

C. Purification

The crude peptide, biotinylated at the amino terminal, was dissolved in 200 mL of a 5% acetonitrile (aqueous) solution containing 0.1% trifluoroacetic acid and then filtered through a 0.22 micron filter. The resulting solution was applied to a 2.2×25 cm reverse phase column of octadecylsilica (Vydac C-18) which had been equilibrated with the same buffer. The peptide was eluted using an 855 minute linear gradient of 7.5–25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated biotinylated peptide gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified peptide was labeled with a fluorescent marker at the C-terminal end for use in the Pandex assay. First, the biotinylate peptide (1.206 g, 0.936 mmol) was dissolved in 100 mL of 0.1M sodium borate, pH 9.5. Then, a solution of 3 g (7.7 mmol) of fluorescein isothiocyanate in 15 mL of dimethyl sulfoxide was added to the reaction mixture in 10 equal portions over two hours. The resulting mixture was allowed to react for one hour after the final addition. The solution was adjusted to pH 3 using 5N hydrochloric acid, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired-product were then combined, frozen and lyophilized to provide 190.2 mg (12%).

Amino acid analysis of the purified peptide gave the following: Asn 1.1; Ser 1.0; Gln 1.1: Pro 1.1; Gly 2.1; Val 0.8; Ile 0.8; Tyr 1.1; Lys 1.0; in agreement with theory. Fast-atom bombardment mass spectrometry gave amolecular ion mass peak of 1678, in agreement with theory.

E. Fluorescence HIV-1 Protease Inhibitor Assay

The following buffers and solutions are used in the Fluorescence HIV-1 Protease Inhibitor Assay:

| MES-ALB Buffer: | 0.05M 4-morpholineethane sulfonic acid, pH 5.5 |
| --- | --- |
| | 0.02M NaCl |
| | 0.002M EDTA |
| | 0.001M DTT |
| | 1.0 mg/mL BSA |
| TBSA Buffer: | 0.02M TRIS |
| | 0.15M NaCl |
| | 1.0 mg/mL BSA |
| Avidin Coated | 0.1% solution of Fluoricon |
| Beads Solution: | Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 μmole of substrate per minute at 37° C. |

To each well of a round bottom, 96-well plate is added 20 μL of the Enzyme Solution followed by 10 μL of the compound to be evaluated in a 20% aqueous dimethylsulfoxide solution. Purified HIV-1 protease was obtained as described above. The resulting solution is incubated for one hour at room temperature and then 20 μL of a solution containing the substrate, prepared above, in MES-ALB buffer (1.5 μl/mL) is added to each well. The solutions are then incubated for 16 hours at room temperature and then each well is diluted with 150 μL of MES-ALB buffer.

To each well of a second round bottom, 96-well Pandex plate is added 25 μL of the Avidin Coated Beads Solution. Then, to each well is added 25 μL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of the present invention which have been tested are set forth below in Table 1. All values have been normalized to a positive control which is [1S-(1R*, 4R*, 5S*)]-N- (1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide.

TABLE 1

Inhibitory Activity of Formula I Compounds

| Example No. | Fluorescence Assay $IC_{50}$ in ng/mL |
| --- | --- |
| Control | 1.0 |
| 33 | 0.7 |
| 36 | 0.3 |
| 37 | 3.6 |
| 38 | 0.5 |
| 39 | 0.6 |
| 40 | 0.45 |
| 41 | 5.5 |
| 42 | 0.45 |
| 43 | N.T.* |
| 44 | 0.15 |
| 45 | N.T.* |
| 46 | 0.92 |
| 47 | 8.1 |
| 48 | $IC_{65}(0.16)$** |
| 49 | 0.7 |

* Not Tested.
** 65% inhibition at 0.16 ng/mL.

We claim:
1. A method of treating HIV infection comprising administering to a primate in need thereof an effective amount of a compound of formula I

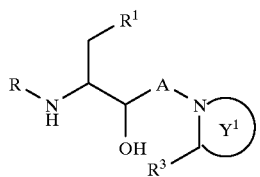

wherein:

R is a group having the formula:

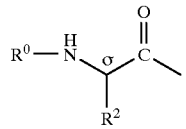

$R^2$ is an amino acid side chain or —$(CH_2)_y$—X—$R^{2a}$; y is 0, 1 or 2;

X is a bond, divalent ($C_2$–$C_4$) alkenyl, divalent ($C_2$–$C_4$) alkynyl, —C(O)—O—, —O—C(O), —C(O)—$NR^{2b}$—, —$NR^{2b}$—C(O)—, —$NR^{2b}$—, —C(O)—, —O—, —S—, —S(O)— or —$S(O)_2$—;

$R^{2a}$ is aryl, unsaturated heterocycle, heterocycle, aryl ($C_1$–$C_4$)alkyl, unsaturated heterocycle ($C_1$–$C_4$) alkyl, heterocycle ($S_1$–$C_4$) alkyl, tetrazolyl, N-($C_1$–$C_4$) alkyltetrazolyl or N-(aryl)tetrazolyl;

$R^{2b}$ is hydrogen or $C_1$–$C_4$ alkyl;

$R^0$ is hydrogen, carbamoyl, formyl, $C_1$–$C_5$ straight or branched alkyl chain bound to a carbonyl moiety, $C_1$–$C_4$ alkoxycarbonyl, —C(O)$CF_3$ or —$S(O)_2$—Z;

Z is $C_1$–$C_6$ alkyl, amino, $C_1$–$C_4$ alkylamino, trifluoromethyl or di($C_1$–$C_4$)alkylamino;

the asymmetric center, σ, is in a non-naturally occurring configuration;

$R^1$ is aryl, $C_5$–$C_7$ cycloalkyl or —S—$R^{1x}$, where $R^{1x}$ is aryl or $C_5$–$C_7$ cycloalkyl;

A is —$CH_2$— or

$Y^1$ is heterocycle;
$R^3$ is a group having the structure:
1) —C(O)—$NR^4R^4$,

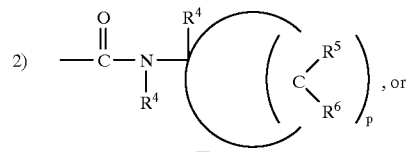

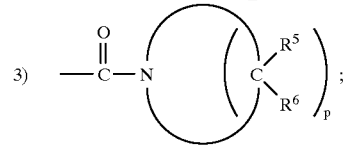

where:
p is 4 or 5;
$R^4$ at each occurrence is independently hydrogen, $C_1$–$C_6$ alkyl or hydroxy($C_1$–$C_4$)alkyl; and
$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy ($C_1$–$C_4$) alkyl, carboxy, $C_1$–$C_4$ alkoxycarbonyl, carbamoyl, N-($C_1$–$C_4$) alkylcarbamoyl, aryl, heterocycle or unsaturated heterocycle; or a pharmaceutically acceptable salt thereof.

2. A method according to claim 1 where the compound is one wherein:

A is —$CH_2$—;
$R^1$ is aryl or —S—$R^{1x}$, where $R^{1x}$ is aryl;
$Y^1$ is decahydro—(4aS, 8aS)—isoquinolinyl or 2'S-pyrrolidinyl; and
$R^3$ is —C(O)—$NR^4R^4$, where $R^4$ is independently and at each occurrence hydrogen or $C_1$–$C_6$ alkyl; or a pharmaceutically acceptable salt thereof.

3. The method according to claim 2 where the compound is one wherein:

$R^1$ is phenyl, phenylthio, naphthyl or naphthylthio;
$R^2$ is —$(CH_2)_y$—X—$R^{2a}$, where
y is 1;
X is a —S—, —S(O)— or —$S(O)_2$—;
$R^{2a}$ is aryl, unsaturated heterocycle, aryl ($C_1$–$C_4$) alkyl, unsaturated heterocycle ($C_1$–$C_4$) alkyl, tetrazolyl, N-($C_1$–$C_4$)alkyltetrazolyl or N-(aryl)tetrazolyl;
$R^0$ is formyl, ethanoyl, —C(O)$CF_3$ or —$S(O)_2$—Z;
Z is methyl or trifluoromethyl;
$Y^1$ is decahydro-(4aS, 8aS)-isoquinolinyl; and
$R^3$ is —C(O)NH(t-butyl);
or a pharmaceutically acceptable salt thereof.

4. A method according to claim 3 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl)amino-7-p-fluoro-phenylsulfonyl]heptyl decahydroisoquinoline-3'-carboxamide
or a pharmaceutically acceptable salt thereof.

5. A method according to claim 3 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl)amino-7-naphth-2-ylsulfonyl]heptyl decahydroisoquinoline-3'-carboxamide;
or a pharmaceutically acceptable salt thereof.

6. A method of treating AIDS comprising administering to a primate in need thereof an effective amount of a compound of formula I

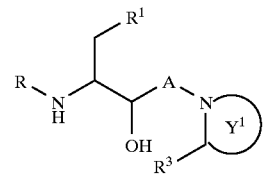

wherein:
R is a group having the formula:

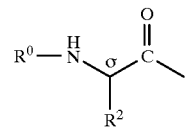

$R^2$ is an amino acid side chain or —$(CH_2)_y$—X—$R^{2a}$; y is 0, 1 or 2;

X is a bond, divalent ($C_2$–$C_4$) alkenyl, divalent ($C_2$–$C_4$) alkynyl, —C(O)—O—, —O—C(O), —C(O)—$NR^{2b}$—, —$NR^{2b}$—C(O)—, —$NR^{2b}$—, —C(O)—, —O—, —S—, —S(O)— or —$S(O)_2$—;

$R^{2a}$ is aryl, unsaturated heterocycle, heterocycle, aryl $(C_1-C_4)$alkyl, unsaturated heterocycle$(C_1-C_4)$alkyl, heterocycle$(S_1-C_4)$alkyl, tetrazolyl, N-$(C_1-C_4)$ alkyltetrazolyl or N-(aryl)tetrazolyl;

$R^{2b}$ is hydrogen or $C_1-C_4$ alkyl;

$R^0$ is hydrogen, carbamoyl, formyl, $C_1-C_5$ straight or branched alkyl chain bound to a carbonyl moiety, $C_1-C_4$ alkoxycarbonyl, —C(O)CF$_3$, or —S(O)$_2$—Z;

Z is $C_1-C_6$ alkyl, amino, $C_1-C_4$ alkylamino, trifluoromethyl or di($C_1-C_4$)alkylamino;

the asymmetric center, σ, is in a non-naturally occurring configuration;

$R^1$ is aryl, $C_5-C_7$ cycloalkyl or —S—$R^{1x}$, where $R^{1x}$ is aryl or $C_5-C_7$ cycloalkyl;

A is —CH$_2$— or

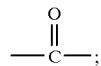

$Y^1$ is heterocycle;
$R^3$ is a group having the structure:
1) —C(O)—NR$^4$R$^4$,

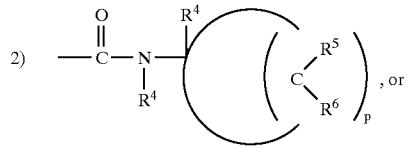

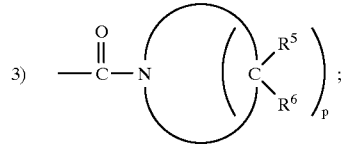

where:
p is 4 or 5;
$R^4$ at each occurrence is independently hydrogen, $C_1-C_6$ alkyl or hydroxy($C_1-C_4$)alkyl; and
$R^5$ and $R^6$ are independently selected from hydrogen, hydroxy, $C_1-C_6$ alkyl, $C_1-C_6$ alkoxy, amino, $C_1-C_4$ alkylamino, hydroxy($C_1-C_4$)alkyl, carboxy, $C_1-C_4$ alkoxycarbonyl, carbamoyl, N-($C_1-C_4$) alkylcarbamoyl, aryl, heterocycle or unsaturated heterocycle; or a pharmaceutically acceptable salt thereof.

7. A method according to claim 6 where the compound is one wherein:
A is —CH$_2$—;
$R^1$ is aryl or —S—$R^{1x}$, where $R^{1x}$ is aryl;
$Y^1$ is decahydro-(4aS, 8aS)-isoquinolinyl or 2'S-pyrrolidinyl; and
$R^3$ is —C(O)—NR$^4$R$^4$, where $R^4$ is independently and at each occurrence hydrogen or $C_1-C_6$ alkyl;
or a pharmaceutically acceptable salt thereof.

8. A method according to claim 7 where the compound is wherein:
$R^1$ is phenyl, phenylthio, naphthyl or naphthylthio;
$R^2$ is —(CH$_2$)$_y$—X—R$^{2a}$, where
y is 1;
X is a —S—, —S(O)— or —S(O)$_2$—;
$R^{2a}$ is aryl, unsaturated heterocycle, aryl($C_1-C_4$)alkyl, unsaturated heterocycle($C_1-C_4$)alkyl, tetrazolyl, N-($C_1-C_4$)alkyltetrazolyl or N-(aryl)tetrazolyl;
$R^0$ is formyl, ethanoyl, —C(O)CF$_3$ or —S(O)$_2$—Z;

Z is methyl or trifluoromethyl;
$Y^1$ is decahydro-(4aS, 8aS)-isoquinolinyl; and
$R^3$ is —C(O)NH(t-butyl);
or a pharmaceutically acceptable salt thereof.

9. A method according to claim 8 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl) amino-7-p-fluoro-phenylsulfonyl]heptyl decahydroisoquinoline-3'-carboxamide
or a pharmaceutically acceptable salt thereof.

10. A method according to claim 8 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl)-amino-7-naphth-2-ylsulfonyl]heptyl decahydroisoquinoline-3'-carboxamide;
or a pharmaceutically acceptable salt thereof.

11. A method of inhibiting HIV replication comprising administering to an HIV infected cell, a cell susceptible to HIV infection or a primate in need thereof an effective amount of a compound of formula I

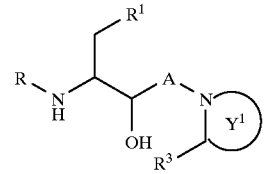

wherein:
R is a group having the formula:

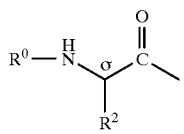

$R^2$ is an amino acid side chain or —(CH$_2$)$_y$—X—R$^{2a}$;
y is 0, 1 or 2;

X is a bond, divalent ($C_2-C_4$) alkenyl, divalent ($C_2-C_4$) alkynyl, —C(O)—O—, —O—C(O), —C(O)—NR$^{2b}$—, —NR$^{2b}$—C(O)—, —NR$^{2b}$—, —C(O)—, —O—, —S—, —S(O)— or —S(O)$_2$—;

$R^{2a}$ is aryl, unsaturated heterocycle, heterocycle, aryl $(C_1-C_4)$ alkyl, unsaturated heterocycle $(C_1-C_4)$ alkyl, heterocycle $(S_1-C_4)$ alkyl, tetrazolyl, N-$(C_1-C_4)$ alkyltetrazolyl or N-(aryl)tetrazolyl;

$R^{2b}$ is hydrogen or $C_1-C_4$ alkyl;

$R^0$ is hydrogen, carbamoyl, formyl, $C_1-C_5$ straight or branched alkyl chain bound to a carbonyl moiety, $C_1-C_4$ alkoxycarbonyl, —C(O)CF$_3$ or —S(O)$_2$—Z;

Z is $C_1-C_6$ alkyl, amino, $C_1-C_4$ alkylamino, trifluoromethyl or di($C_1-C_4$)alkylamino;

the asymmetric center, σ, is in a non-naturally occurring configuration;

$R^1$ is aryl, $C_5-C_7$ cycloalkyl or —S—$R^{1x}$, where $R^{1x}$ is aryl or $C_5-C_7$ cycloalkyl;

A is —CH$_2$— or

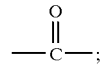

$Y^1$ is heterocycle;
$R^3$ is a group having the structure:
1) —C(O)—NR$^4$R$^4$, 2) 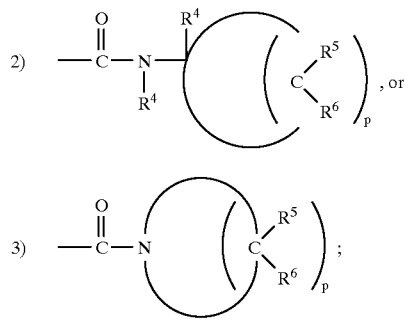, or

3)

where:
p is 4 or 5;
$R^4$ at each occurrence is independently hydrogen, $C_1$–$C_6$ alkyl or hydroxy($C_1$–$C_4$)alkyl; and
$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkyl, carboxy, $C_1$–$C_4$ alkoxycarbonyl, carbamoyl, N-($C_1$–$C_4$) alkylcarbamoyl, aryl, heterocycle or unsaturated heterocycle; or a pharmaceutically acceptable salt thereof.

12. A method according to claim 11 where the compound is one wherein:
A is —CH$_2$—;
$R^1$ is aryl or —S—R$^{1x}$, where R$^{1x}$ is aryl;
$Y^1$ is decahydro-(4aS, 8aS)-isoquinolinyl or 2'S-pyrrolidinyl; and
$R^3$ is —C(O)—NR$^4$R$^4$, where $R^4$ is independently and at each occurrence hydrogen or $C_1$–$C_6$ alkyl;
or a pharmaceutically acceptable salt thereof.

13. A method according to claim 12 where the compound is wherein:
$R^1$ is phenyl, phenylthio, naphthyl or naphthylthio;
$R^2$ is —(CH$_2$)$_y$—X—R$^{2a}$, where
y is 1;
X is a —S—, —S(O)— or —S(O)$_2$—;
$R^2$a is aryl, unsaturated heterocycle, aryl ($C_1$–$C_4$) alkyl, unsaturated heterocycle ($C_1$–$C_4$) alkyl, tetrazolyl, N-($C_1$–$C_4$)alkyltetrazolyl or N-(aryl)tetrazolyl;
$R^0$ is formyl, ethanoyl, —C(O)CF$_3$ or —S(O)$_2$—Z;
Z is methyl or trifluoromethyl;
$Y^1$ is decahydro-(4aS, 8aS)-isoquinolinyl; and
$R^3$ is —C(O)NH(t-butyl);
or a pharmaceutically acceptable salt thereof.

14. A method according to claim 13 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl) amino-7-p-fluoro-phenylsulfonyl]heptyl decahydroisoquinoline-3'-carboxamide
or a pharmaceutically acceptable salt thereof.

15. A method according to claim 13 where the compound is [2R-(2R*,3S*,6S*,3'S*,4a'S*,8a'S*)]-N(t-Butyl)-2'-[2-hydroxy-3-phenylmethyl-4-aza-5-oxo-6-N(methylsulfonyl) amino-7-naphth-2-ylsulfonyl]heptyl decahydroisoquinoline-3'-carboxamide
or a pharmaceutically acceptable salt thereof.

16. The method according to claim 1, wherein
$R^1$ is phenyl, phenylthio, naphthyl or naphthylthio;
$R^2$ is —(CH$_2$)$_y$—X—R$^{2a}$, where
y is 1;
X is a —S—, —S(O)— or —S(O)$_2$—;
$R^{2a}$ is aryl, aryl (C$_1$)alkyl;
$R^0$ is ethanoyl or —S(O)$_2$—Z;
Z is methyl;
$Y^1$ is decahydro-(4aS, 8aS)-isoquinolinyl; and
$R^3$ is —C(O)NH(t-butyl);
or a pharmaceutically acceptable salt thereof.

17. The method according to claim 16, wherein $R^0$ is —S(O)$_2$—Z.

18. The method according to claim 16, wherein $R^1$ is phenyl.

19. The method according to claim 1, wherein $R^2$ is —(CH$_2$)$_y$—X—R$^{2a}$;
y is 0, 1 or 2;
X is a bond, divalent (C$_2$–C$_4$) alkenyl, divalent (C$_2$–C$_4$) alkynyl, —C(O)—O—, —O—C(O), —C(O)—NR$^{2b}$—, —NR$^{2b}$—C(O)—, —NR$^{2b}$—, —C(O)—, —O—, —S—, —S(O)— or —S(O)$_2$—;
$R^{2a}$ is aryl, unsaturated heterocycle, heterocycle, aryl (C$_1$–C$_4$) alkyl, unsaturated heterocycle(C$_1$–C$_4$)alkyl, heterocycle(S$_1$–C$_4$)alkyl, tetrazolyl, N-(C$_1$–C$_4$) alkyltetrazolyl or N-(aryl)tetrazolyl;
$R^{2b}$ is hydrogen or C$_1$–C$_4$ alkyl.

20. The method according to claim 6, wherein
$R^1$ is phenyl, phenylthio, naphthyl or naphthylthio;
$R^2$ is —(CH$_2$)$_y$—X—R$^{2a}$, where
y is 1;
X is a —S—, —S(O)— or —S(O)$_2$—;
$R^{2a}$ is aryl, aryl (C$_1$)alkyl;
$R^0$ is ethanoyl or —S(O)$_2$—Z;
Z is methyl;
$Y^1$ is decahydro-(4aS, 8aS)-isoquinolinyl; and
$R^3$ is —C(O)NH(t-butyl);
or a pharmaceutically acceptable salt thereof.

21. The method according to claim 20, wherein $R^0$ is —S(O)$_2$—Z.

22. The method according to claim 20, wherein $R^1$ is phenyl.

23. The method according to claim 6, wherein $R^2$ is —(CH$_2$)$_y$—X—
y is 0, 1 or 2;
X is a bond, divalent (C$_2$–C$_4$) alkenyl, divalent (C$_2$–C$_4$) alkynyl, —C(O)—O—, —O—C(O), —C(O)—NR$^{2b}$—, —NR$^{2b}$—C(O)—, —NR$^{2b}$—, —C(O)—, —O—, —S—, —S(O)— or —S(O)$_2$—;
$R^{2a}$ is aryl, unsaturated heterocycle, heterocycle, aryl (C$_1$–C$_4$)alkyl, unsaturated heterocycle (C$_1$–C$_4$) alkyl, heterocycle (S$_1$–C$_4$) alkyl, tetrazolyl, N-(C$_1$–C$_4$) alkyltetrazolyl or N-(aryl)tetrazolyl;
$R^{2b}$ is hydrogen or C$_1$–C$_4$ alkyl.

24. The method according to claim 11, wherein
$R^1$ is phenyl, phenylthio, naphthyl or naphthylthio;
$R^2$ is (CH$_2$)$_y$—X—R$^{2a}$, where
y is 1;
X is a —S—, —S(O)— or —S(O)$_2$—;
$R^{2a}$ is aryl, aryl (C$_1$)alkyl;
$R^0$ is ethanoyl or —S(O)$_2$—Z;
Z is methyl;
$Y^1$ is decahydro-(4aS,8aS)-isoquinolinyl; and
$R^3$ is —C(O)NH(t-butyl);
or a pharmaceutically acceptable salt thereof.

25. The method according to claim 24, wherein $R^0$ is —S(O)$_2$—Z.

26. The method according to claim 24, wherein $R^1$ is phenyl.

27. The method according to claim 11, wherein $R^2$ is —$(CH_2)_y$—X—$R^{2a}$;

y is 0, 1 or 2;

X is a bond, divalent ($C_2$–$C_4$) alkenyl, divalent ($C_2$–$C_4$) alkynyl, —C(O)—C—, —O—C(O), —C(O)—$NR^{2b}$—, —$NR^{2b}$—C(O)—, —$NR^{2b}$—, —C(O)—, —O—, —S—, —S(O)— or —S(O)$_2$—;

$R^{2a}$ is aryl, unsaturated heterocycle, heterocycle, aryl ($C_1$–$C_4$)alkyl, unsaturated heterocycle ($C_1$–$C_4$) alkyl, heterocycle ($S_1$–$C_4$) alkyl, tetrazolyl, N-($C_1$–$C_4$) alkyltetrazolyl or N-(aryl)tetrazolyl;

$R^{2b}$ is hydrogen or $C_1$–$C_4$ alkyl.

* * * * *